(12) United States Patent
Ghosh et al.

(10) Patent No.: US 9,002,454 B2
(45) Date of Patent: Apr. 7, 2015

(54) TRACKING PACING EFFECTIVENESS BASED ON WAVEFORM FEATURES

(71) Applicant: Medtronic, Inc., Minneapolis, MN (US)

(72) Inventors: Subham Ghosh, Blaine, MN (US); Jeffrey M Gillberg, Coon Rapids, MN (US); Aleksandre T Sambelashvili, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 66 days.

(21) Appl. No.: 13/717,896

(22) Filed: Dec. 18, 2012

(65) Prior Publication Data

US 2014/0114372 A1    Apr. 24, 2014

Related U.S. Application Data

(60) Provisional application No. 61/580,058, filed on Dec. 23, 2011.

(51) Int. Cl.
*A61N 1/37* (2006.01)
*A61N 1/368* (2006.01)

(52) U.S. Cl.
CPC . *A61N 1/371* (2013.01); *A61N 1/37* (2013.01)

(58) Field of Classification Search
USPC ................................... 607/4, 15, 28
See application file for complete search history.

(56) References Cited

U.S. PATENT DOCUMENTS

| | | | |
|---|---|---|---|
| 4,374,382 A | 2/1983 | Markowitz | |
| 5,117,824 A | 6/1992 | Keimel et al. | |
| 5,545,186 A | 8/1996 | Olson et al. | |
| 5,755,736 A | 5/1998 | Gillberg et al. | |
| 6,381,493 B1 | 4/2002 | Stadler et al. | |
| 6,393,316 B1 | 5/2002 | Gillberg et al. | |
| 7,286,876 B2 | 10/2007 | Yonce et al. | |
| 7,664,550 B2 | 2/2010 | Eick et al. | |
| 7,912,544 B1 | 3/2011 | Min et al. | |
| 7,912,554 B2 | 3/2011 | Capuano et al. | |
| 7,925,346 B1 | 4/2011 | Go | |
| 8,160,700 B1 | 4/2012 | Ryu et al. | |
| 2003/0187482 A1 | 10/2003 | Pastore et al. | |
| 2004/0220635 A1 | 11/2004 | Burnes | |
| 2006/0224198 A1 | 10/2006 | Dong et al. | |
| 2009/0005832 A1 | 1/2009 | Zhu et al. | |
| 2009/0270937 A1 | 10/2009 | Yonce et al. | |

(Continued)

FOREIGN PATENT DOCUMENTS

| EP | 2 016 976 A1 | 1/2009 |
|---|---|---|
| EP | 2188011 B1 | 5/2011 |

(Continued)

OTHER PUBLICATIONS

Hayes et al., "Cardiac resynchronization therapy and the relationship of percent biventricular pacing to symptoms and survival," *Heart Rhythm*, Sep. 2011; 8(9):1469-1475.

(Continued)

*Primary Examiner* — Carl H Layno
*Assistant Examiner* — Jon Eric C Morales
(74) *Attorney, Agent, or Firm* — Carol F. Barry

(57) ABSTRACT

Methods and/or devices may be configured to track effectiveness of pacing therapy by monitoring two or more electrical vectors of the patient's heart during pacing therapy and analyzing at least one feature of a morphological waveform within each of the two or more electrical vectors.

20 Claims, 21 Drawing Sheets

(56) References Cited

U.S. PATENT DOCUMENTS

| | | |
|---|---|---|
| 2009/0318995 A1 | 12/2009 | Keel et al. |
| 2011/0022112 A1 | 1/2011 | Min |
| 2011/0054559 A1 | 3/2011 | Rosenberg et al. |
| 2011/0054560 A1 | 3/2011 | Rosenberg et al. |
| 2011/0093031 A1 | 4/2011 | Yu et al. |
| 2012/0185012 A1 | 7/2012 | Ryu et al. |
| 2013/0165983 A1* | 6/2013 | Ghosh et al. ............ 607/4 |

FOREIGN PATENT DOCUMENTS

| | | |
|---|---|---|
| EP | 2349468 | 8/2011 |
| WO | WO 2005/056108 A2 | 6/2005 |
| WO | WO 2010/039501 A1 | 4/2010 |

OTHER PUBLICATIONS

International Search Report and Written Opinion issued Jun. 18, 2013, in Europe, Patent Application No. PCT/US2012/070541, filed Dec. 19, 2012; 12 pages.

Kamath et al, "The Utility of 12-Lead Holter Monitoring in Patients with Permanent Atrial Fibrillation for the Identification of Nonresponders After Cardiac Resynchronization Therapy," *Journal of the American College of Cardiology*, Mar. 24, 2009; 53(12): 1050-1055.

Steinhaus BM., "Estimating cardiac transmembrane activation and recovery times from unipolar and bipolar extracellular electrograms: a simulation study," *Circulation Research*, 1989, 64:449-462.

\* cited by examiner

TRACKING PACING EFFECTIVENESS BASED ON WAVEFORM FEATURES

CROSS-REFERENCE TO RELATED APPLICATIONS

This application claims the benefit of U.S. Provisional Application No. 61/580,058, filed on Dec. 23, 2011. The disclosure of the above application is incorporated herein by reference in its entirety.

BACKGROUND OF THE INVENTION

The disclosure herein relates to methods and systems for tracking pacing effectiveness by monitoring the electrical vectors of the patient's heart during pacing therapy and analyzing one or more features within the monitored electrical vectors.

Implantable medical devices (IMDs) are capable of utilizing pacing therapies, such as cardiac resynchronization therapy (CRT), to maintain hemodynamic benefits to patients. Pacing therapy may be delivered from an implantable generator, through a lead, and into the patient's heart. Basic programmable pacing parameters include pacing amplitude, pacing rate, pulse duration, and pacing pathway or vector (e.g., bipolar such as a lead tip electrode to a lead ring electrode, etc. or unipolar such as a lead tip electrode to IMD casing, or housing), which all may be configured to ensure effective therapy to the patient.

CRT may improve cardiac function and clinical outcomes through the use of permanent biventricular (BV) and left ventricular (LV) pacing. The proportion of ventricular paced beats with respect to the total number of paced and sensed beats has been associated with CRT efficacy. The proportion may be referred to as a BV or LV pacing ratio, which is the number of paced heart beats divided by the total number of heart beats. Present devices including diagnostics may track the pacing ratio.

Existing methods of morphology analysis may use template matching algorithms like WAVELET (e.g., for distinguishing supraventricular tachycardia from ventricular tachycardia). Such existing methods of morphology analysis may not be practical since such algorithms may be computationally intensive for an IMD to execute, especially on a beat-by-beat basis. Also, the electrogram (EGM) waveforms in CRT devices may be corrupted by pacing artifacts, which may make detailed template matching methods unreliable for accurate rhythm classification.

SUMMARY

Diagnostic methods and systems that can utilize a feature-based algorithm for beat-to-beat rhythm classification for use in determining pacing effectiveness in CRT pacing are described herein. For example, exemplary systems and methods described herein relate to monitoring two or more electrical vectors of a patient's heart during pacing therapy, analyzing whether each paced event has a predetermined level of effectiveness, and tracking a pacing effectiveness ratio based on the analysis.

Generally, the disclosure herein, in or more embodiments, describes evaluation of one or more gross morphological features (e.g., f1, f2, . . . fn) of a ventricular electrogram waveform during CRT pacing (e.g., a morphological waveform within a predetermined, or selected, time period after the delivery of pacing stimulus) with effective capture at programmed settings (e.g., A-V delay, V-V delay, etc.). Exemplary features may include peak-to-peak amplitude, peak slope, a peak number based on the ratio of the positive peak and the negative peak, order of timing of the positive peak and the negative peak, etc. Mean value and variability (e.g., standard deviation) of one or more of these features in baseline conditions of CRT pacing may be computed and stored over a selected number of cardiac cycles. For one or more exemplary devices capable of employing both LV only fusion pacing and biventricular pacing, two sets of features may be collected: one set of features for the LV only pacing during adaptive (or programmed) A-V delays; and another set of features for biventricular pacing at a short A-V delay. One or more exemplary devices may then be programmed to monitor the patient's cardiac rhythm (e.g., daily during selected periods of time during the day, during certain rhythm conditions like atrial tachycardia/atrial fibrillation, etc.) by comparing morphological features of an electrogram waveform of paced beats (e.g., a morphological waveform within a predetermined, or selected, time period after the delivery of pacing stimulus) to the stored features on a beat-by-beat basis. If one or more features of a morphological waveform corresponding to a particular paced beat (e.g., a morphological waveform within a predetermined, or selected, time period after the delivery of pacing stimulus) do not match the corresponding stored feature for the particular pacing therapy delivered (e.g., LV only pacing, BV pacing, etc.) within allowed thresholds of variability, then the particular paced beat may be classified as inconsistent or ineffective. Conversely, if a selected number of features of a morphological waveform corresponding to a particular paced beat do match the corresponding stored feature for the particular pacing therapy delivered (e.g., LV only pacing, BV pacing, etc.) within allowed thresholds of variability, then the particular paced beat may be classified as consistent or effective (e.g., as having a predetermined level of effectiveness).

In one or more embodiments, a percentage of consistent paced beats (e.g., a pacing effectiveness ratio) may be computed by dividing the number of paced beats found consistent or effective (e.g., as having a predetermined level of effectiveness) by the number of paced beats monitored. A high value of the percentage of consistency/effectiveness may indicate that no, or minimal, rhythm changes have occurred, or taken place. A low value of the percentage of consistency/effectiveness may indicate that a change (e.g., a major change) has occurred in paced rhythm. Further, if the percentage of consistency/effectiveness falls below a set threshold (e.g., 90%) for a period of consecutive days, a follow-up action may be initiated such as triggering an alert (e.g., a wireless transmission) urging a prompt device check. Changes (e.g., major changes) in a paced rhythm may occur, or take place, due to loss of capture, intermittent capture, frequent ectopies interfering with pacing, junctional rhythm, variable intrinsic A-V conduction patterns, or any other source of undesirable fusion.

One exemplary system for tracking effectiveness of pacing therapy to a patient may include a therapy delivery module configured to deliver pacing therapy to a patient's heart, sensing apparatus configured to monitor electrical activity of the patient's heart (e.g., the sensing apparatus may include a plurality of electrodes), a sensing module coupled to the sensing apparatus and configured to monitor two or more electrical vectors of the patient's heart using the plurality of electrodes of the sensing apparatus during pacing therapy, and a control module coupled to the therapy delivery module and to the sensing module. The control module may be configured to initiate the delivery of pacing therapy to the patient's heart over a plurality of heartbeats and to monitor two or more electrical vectors of the patient's heart during pacing therapy for each paced event of a plurality of paced events occurring over a period of time. Monitoring the two or more electrical vectors may include sensing a morphologic waveform corresponding to the paced event at each electrical vector of the two or more electrical vectors using a different pair of electrodes of the plurality of electrodes (e.g., each electrode of the different pairs of electrodes used to sense the two or more electrical vectors are not used for pacing therapy). In at least one embodiment, at least one electrical vector of the two or more electrical vectors is sensed using an electrode located proximate the patient's right ventricle and a housing electrode located on a housing of the implantable medical device. The control module may be further configured to analyze whether each paced event of the plurality of paced events has a predetermined level of effectiveness based on at least one feature of the sensed morphologic waveform for each electrical vector of the two or more monitored electrical vectors and track a pacing effectiveness ratio, the pacing effectiveness ratio being the ratio between the amount of paced events over time having a predetermined level of effectiveness and the number of paced events.

One exemplary method of tracking effectiveness of pacing therapy provided using an implantable medical device may include delivering pacing therapy to a patient's heart using one or more pacing electrodes of an implantable medical device (e.g., the pacing therapy may be delivered over a plurality of heartbeats) and monitoring two or more electrical vectors of the patient's heart during pacing therapy for each paced event of a plurality of paced events occurring over a period of time. Monitoring the two or more electrical vectors may include sensing a morphologic waveform corresponding to the paced event at each electrical vector of the two or more electrical vectors using a different pair of electrodes of the implantable medical device. The exemplary method may further include analyzing, using the implantable medical device, whether each paced event of the plurality of paced events has a predetermined level of effectiveness based on at least one feature of the sensed morphologic waveform for each electrical vector of the two or more monitored electrical vectors and tracking, using the implantable medical device, a pacing effectiveness ratio, the pacing effectiveness ratio being the ratio between the amount of paced events over time having a predetermined level of effectiveness and the number of paced events.

In one or more embodiments of the systems and methods described herein, the control modules may be further configured to execute and/or the methods may further include collecting at least one reference feature of a reference morphological waveform corresponding to a known effectively paced event for each electrical vector of the two or more monitored electrical vectors, and analyzing whether each paced event of the plurality of paced events has a predetermined level of effectiveness may include comparing the at least one feature of the sensed morphological waveform to the at least one feature of the reference morphological waveform. In at least one embodiment, collecting at least one reference feature of a reference morphological waveform corresponding to a known effectively paced event may include collecting at least one reference feature of a reference morphological waveform corresponding to a known effectively paced event for a plurality of sensed atrioventricular delays for each electrical vector of the two or more monitored electrical vectors.

In one or more embodiments, the at least one feature includes: an absolute value of a maximum value of the sensed morphological waveform; an absolute value of a minimum value of the sensed morphological waveform; a max time value representing when a maximum value of the sensed morphological waveform occurs; and a min time value representing when a minimum value of the sensed morphological waveform occur.

In one or more embodiments of the systems and methods described herein, analyzing whether each paced event of the plurality of paced events has a predetermined level of effectiveness may include classifying the paced event as an effectively paced event if, for each electrical vector of the two or more electrical vectors: the lesser of the absolute value of the maximum value and the absolute value of value of the minimum value is less than a selected threshold value; and the absolute value of the minimum value is greater than the absolute value of value of the maximum value. In at least one embodiment, the amount of fusion events, pseudo-fusion events, and/or unknown events may be tracked over time.

In one or more embodiments of the systems and methods described herein, analyzing whether each paced event of the plurality of paced events has a predetermined level of effectiveness may include classifying the paced event as one of an effectively paced event, a pseudo-fusion event, a fusion event, and an unknown event based on one or more of the absolute value of the maximum value, the absolute value of the minimum value, the max time value, and the min time value. For example, the paced event may be classified as a pseudo-fusion event if, for each electrical vector of the two or more electrical vectors: the lesser of the absolute value of the maximum value and the absolute value of value of the minimum value is less than a selected threshold value, and the absolute value of the maximum value is greater than the absolute value of value of the minimum value. Further, for example, the paced event may be classified as a fusion event if, for each electrical vector of the two or more electrical vectors: the lesser if the absolute value of the maximum value and the absolute value of value of the minimum value is greater than a selected threshold value, and the max time value occurs before the min time value. Still further, for example, the paced event may be classified as an effectively paced event if, for each electrical vector of the two or more electrical vectors: a ratio of the absolute value of the maximum value to the absolute value of the minimum value is less than or equal to 2, and the max time value occurs before the min time value.

In one or more embodiments of the systems and methods described herein, the control modules may be further configured to execute and/or the methods may further include initiating an alert if the effectiveness ratio drops below an effectiveness threshold value over a selected period of time.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
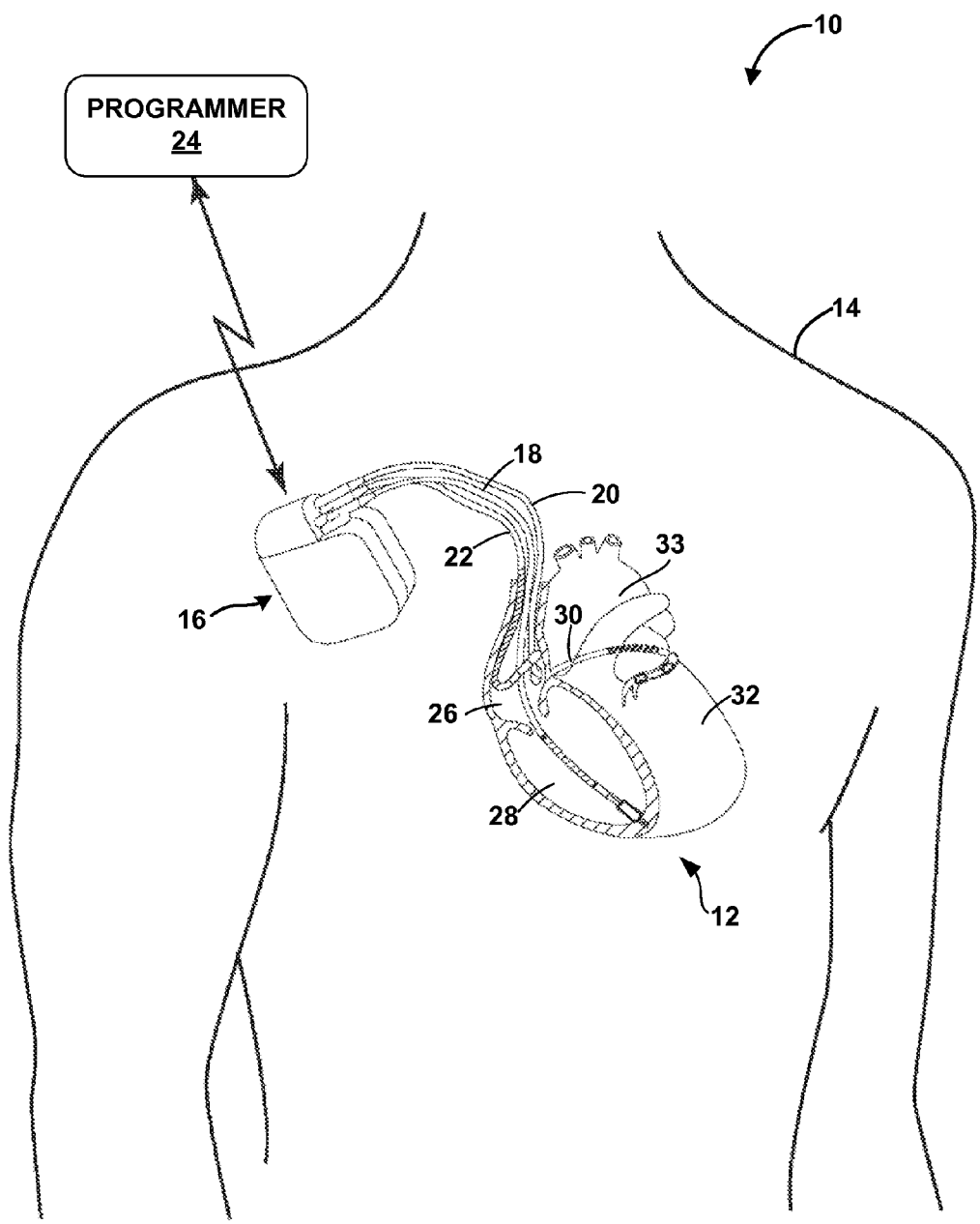
FIG. 1 is a diagram of an exemplary system including an exemplary implantable medical device (IMD).

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods, devices, and systems shall be described with reference to FIGS. 1-16. It will be apparent to one skilled in the art that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

FIG. 1 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22 and a programmer 24. The IMD 16 may be, e.g., an implantable pacemaker, cardioverter, and/or defibrillator, that provides electrical signals to the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., pulse wide, amplitude, voltage, burst length, etc. Further, the IMD 16 may be operable to use various electrode configurations to deliver pacing therapy, which may be unipolar or bipolar. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

In some examples, a programmer 24, which may be a handheld computing device or a computer workstation, may be used by a user, such as a physician, technician, another clinician, and/or patient, to communicate with the IMD 16 (e.g., to program the IMD 16). For example, the user may interact with the programmer 24 to retrieve information concerning one or more detected or indicated faults associated within the IMD 16 and/or the pacing therapy delivered therewith. The IMD 16 and the programmer 24 may communicate via wireless communication using any techniques known in the art. Examples of communication techniques may include, e.g., low frequency or radiofrequency (RF) telemetry, but other techniques are also contemplated.

Figure 2:
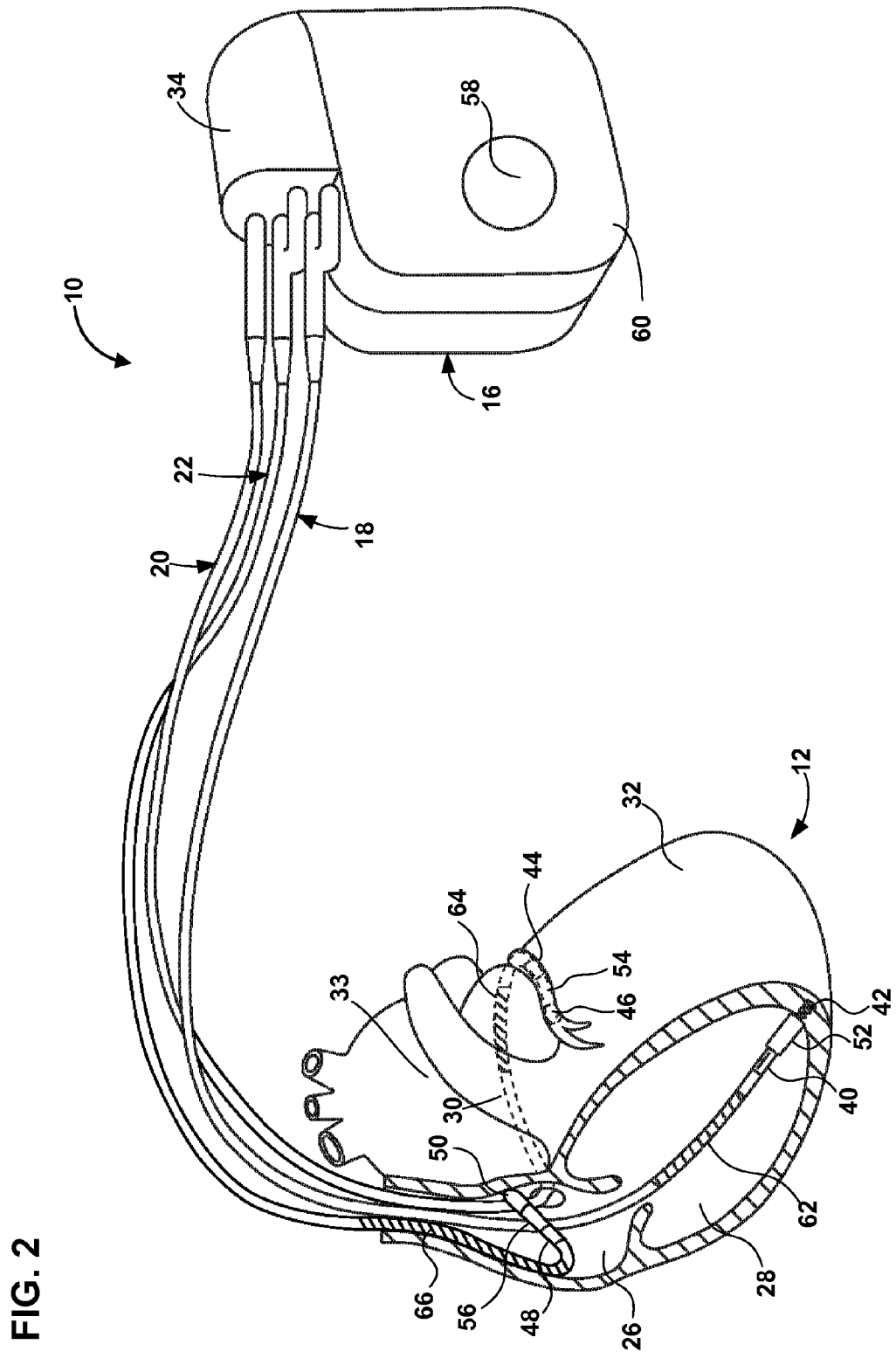
FIG. 2 is a diagram of the exemplary IMD of FIG. 1.

FIG. 2 is a conceptual diagram illustrating the IMD 16 and the leads 18, 20, 22 of therapy system 10 of FIG. 1 in more detail. The leads 18, 20, 22 may be electrically coupled to a therapy delivery module (e.g., for delivery of pacing therapy), a sensing module (e.g., one or more electrodes to sense or monitor electrical activity of the heart 12 for use in determining effectiveness of pacing therapy), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, the bipolar electrodes 44, 46 are located proximate to a distal end of the lead 20 and the bipolar electrodes 48, 50 are located proximate to a distal end of the lead 22.

The electrodes 40, 44, 48 may take the form of ring electrodes, and the electrodes 42, 46, 50 may take the form of extendable helix tip electrodes mounted retractably within the insulative electrode heads 52, 54, 56, respectively. Each of the electrodes 40, 42, 44, 46, 48, 50 may be electrically coupled to a respective one of the conductors (e.g., coiled and/or straight) within the lead body of its associated lead 18, 20, 22, and thereby coupled to respective ones of the electrical contacts on the proximal end of the leads 18, 20, 22.

The electrodes 40, 42, 44, 46, 48, 50 may further be used to sense electrical signals (e.g., morphological waveforms within electrograms (EGM)) attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 46, 48, 50 to cause depolarization of cardiac tissue of the patient's heart 12. In some examples, as illustrated in FIG. 2, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 46, 48, 50 may be used for unipolar sensing or pacing in combination with housing electrode 58. In other words, any of electrodes 40, 42, 44, 46, 48, 50, 58 may be used in combination to form a sensing vector, e.g., a sensing vector that may be used to evaluate and/or analysis the effectiveness of pacing therapy. Further, any of electrodes 40, 42, 44, 46, 48, 50, 58, which are not being used to deliver pacing therapy, may be used to sense electrical activity during pacing therapy (e.g., sensing morphological waveforms for use in determining pacing effectiveness based on one or more features within morphological waveforms). As described in further detail with reference to FIG. 3, the housing 60 may enclose a therapy delivery module that may include a stimulation generator for generating cardiac pacing pulses and defibrillation or cardioversion shocks, as well as a sensing module for monitoring the patient's heart rhythm.

The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity during pacing therapy (e.g., for use in analyzing pacing therapy effectiveness) and may be used in combination with any of electrodes 40, 42, 44, 46, 48, 50, 58. In at least one embodiment, the RV elongated electrode 62 may be used to sense electrical activity of a patient's heart during the delivery of pacing therapy (e.g., in combination with the housing electrode 58 forming a RV elongated, coil, or defibrillation electrode-to-housing electrode vector).

The configuration of the exemplary therapy system 10 illustrated in FIGS. 1-2 is merely one example. In other examples, the therapy system may include epicardial leads and/or patch electrodes instead of or in addition to the transvenous leads 18, 20, 22 illustrated in FIG. 1. Further, in one or more embodiments, the IMD 16 need not be implanted within the patient 14. For example, the IMD 16 may deliver defibrillation shocks and other therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 1-2. Still further, other therapy systems may include a single lead that extends from the IMD 16 into the right atrium 26 or the right ventricle 28, or two leads that extend into a respective one of the right atrium 26 and the right ventricle 28.

Figure 3:
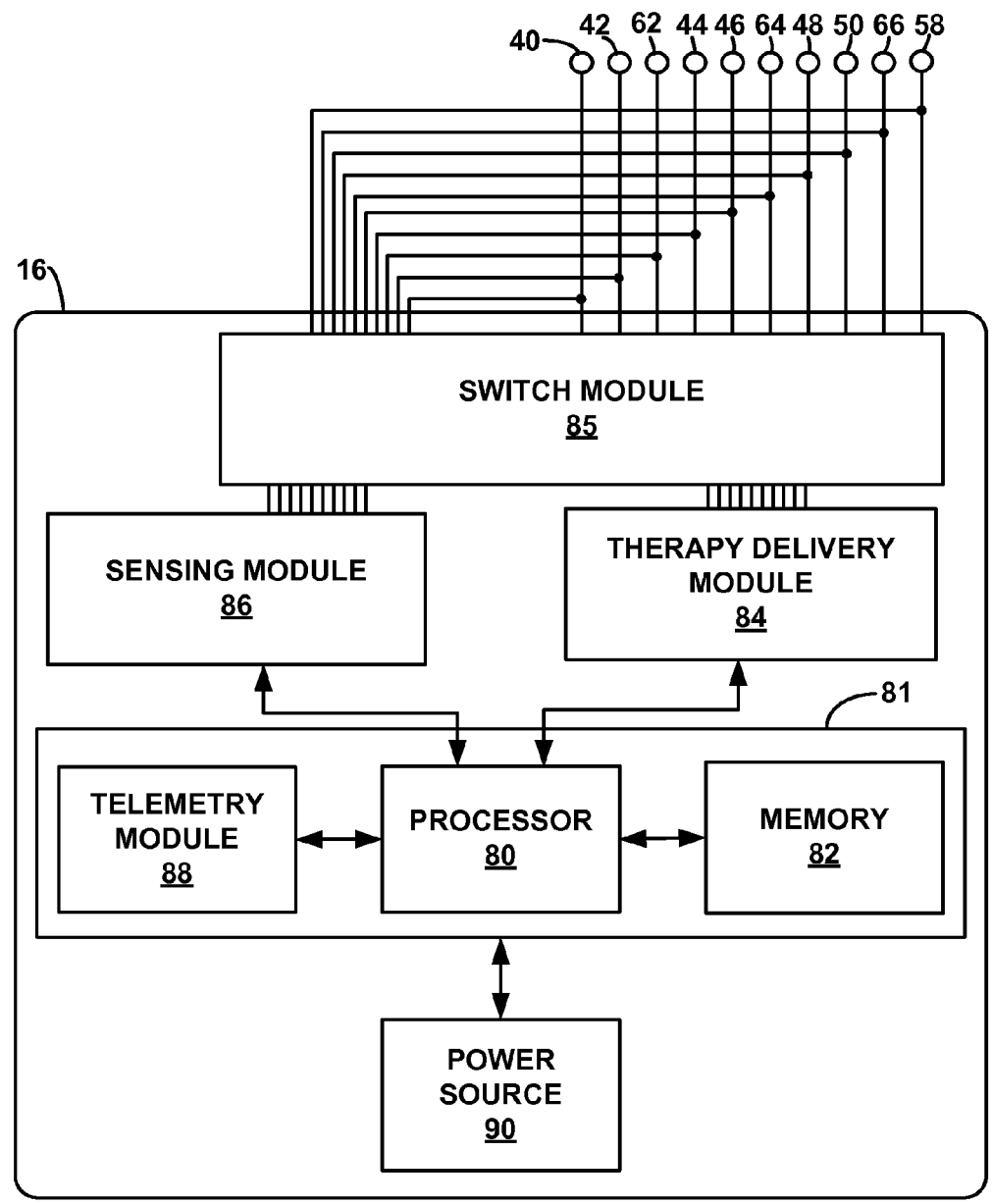
FIG. 3 is a block diagram of an exemplary IMD, e.g., the IMD of FIGS. 1-2.

FIG. 3 is a functional block diagram of one exemplary configuration of the IMD 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random access memory (RAM), read-only memory (ROM), non-volatile RAM (NVRAM), electrically-erasable programmable ROM (EEPROM), flash memory, and/or any other digital media.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control the therapy delivery module 84 to deliver electrical stimulus such as, e.g., pacing pulses with the amplitudes, pulse widths, frequency, or electrode polarities specified by the selected one or more therapy programs (e.g., pacing therapy programs, pacing recovery programs, capture management programs, etc.). As shown, the therapy delivery module 84 is electrically coupled to electrodes 40, 42, 44, 46, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 46, 48, 50, 58, 62, 64, 66.

For example, therapy delivery module 84 may deliver pacing stimulus (e.g., pacing pulses) via ring electrodes 40, 44, 48 coupled to leads 18, 20, and 22, respectively, and/or helical tip electrodes 42, 46, and 50 of leads 18, 20, and 22, respectively. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 46, 48, 50, 58, 62, 64, 66 (e.g., a pair of electrodes for delivery of therapy to a pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 46, 48, 50, 58, 62, 64, 66 to monitor electrical activity of the heart 12, e.g., electrocardiogram (ECG)/electrogram (EGM) signals, etc. The ECG/EGM signals may be used to analyze of a plurality of paced events. More specifically, one or more morphological features of each paced event within the ECG/EGM signals may be used to determine whether each paced event has a predetermined level effectiveness. The ECG/EGM signals may be further used to monitor heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may be also be used with the sensing module 86 to select which of the available electrodes are used to, e.g., sense electrical activity of the patient's heart (e.g., one or more electrical vectors of the patient's heart using any combination of the electrodes 40, 42, 44, 46, 48, 50, 58, 62, 64, 66). In some examples, the control module 81 may select the electrodes that function as sensing electrodes via the switch module within the sensing module 86, e.g., by providing signals via a data/address bus. In some examples, the sensing module 86 may include one or more sensing channels, each of which may include an amplifier. In some examples, sensing module 86 includes a channel that includes an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an electrogram (EGM). In some examples, the storage of such EGMs in memory 82 may be under the control of a direct memory access circuit. The control module 81 (e.g., using the processor 80) may employ digital signal analysis techniques to characterize the digitized signals stored in memory 82 to analyze and/or classify one or more morphological waveforms of the EGM signals to determine pacing therapy effectiveness. For example, the processor 80 may be configured to determine, or obtain, one more features of one or more sensed morphological waveforms within one of more electrical vectors of the patient's heart and store the one or more features within the memory 82 for use in determining effectiveness of pacing therapy at a later time.

If IMD 16 is configured to generate and deliver pacing pulses to the heart 12, the control module 81 may include a pacer timing and control module, which may be embodied as hardware, firmware, software, or any combination thereof. The pacer timing and control module may include one or more dedicated hardware circuits, such as an ASIC, separate from the processor 80, such as a microprocessor, and/or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

Intervals defined by the pacer timing and control module within control module 81 may include atrial and ventricular pacing escape intervals, refractory periods during which sensed P-waves and R-waves are ineffective to restart timing of the escape intervals, and/or the pulse widths of the pacing pulses. As another example, the pacer timing and control module may define a blanking period, and provide signals from sensing module 86 to blank one or more channels, e.g., amplifiers, for a period during and after delivery of electrical stimulation to the heart 12. The durations of these intervals may be determined in response to stored data in memory 82. The pacer timing and control module of the control module 81 may also determine the amplitude of the cardiac pacing pulses.

During pacing, escape interval counters within the pacer timing/control module may be reset upon sensing of R-waves and P-waves. Therapy delivery module 84 (e.g., including a stimulation generator) may include one or more pacing output circuits that are coupled, e.g., selectively by the switch module 85, to any combination of electrodes 40, 42, 44, 46, 48, 50, 58, 62, or 66 appropriate for delivery of a bipolar or unipolar pacing pulse to one of the chambers of heart 12. The control module 81 may reset the escape interval counters upon the generation of pacing pulses by therapy delivery module 84, and thereby control the basic timing of cardiac pacing functions, including anti-tachyarrhythmia pacing.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as the programmer 24 as described herein with respect to FIG. 1. For example, under the control of the processor 80, the telemetry module 88 may receive downlink telemetry from and send uplink telemetry to the programmer 24 with the aid of an antenna, which may be internal and/or external. The processor 80 may provide the data to be uplinked to the programmer 24 and the control signals for the telemetry circuit within the telemetry module 88, e.g., via an address/data bus. In some examples, the telemetry module 88 may provide received data to the processor 80 via a multiplexer. In at least one embodiment, the telemetry module 88 may be configured to transmit an alarm, or alert, if the pacing therapy becomes ineffective or less effective (e.g., does not have a predetermined level of effectiveness).

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

A pacing (e.g., for LV and/or BV pacing) ratio, which is the number of paced heart beats divided by the total number of heart beats, may be a useful metric for evaluating the effectiveness of CRT but, in many cases, it may be misleading because a high pacing ratio may not necessarily mean that CRT is effective if, e.g., ventricular pacing fails to properly alter electrical activation patterns. Automatic beat-to-beat analysis of the evoked response (e.g., paced QRS complexes) in monitored EGM signals may be used to determine whether the paced heartbeat was effectively paced, and hence, to provide more resolution to a pacing ratio. For example, the heartbeats that were paced but determined to not be effectively paced (e.g., depending on the degree of fusion between intrinsic and paced activation, etc.) may be excluded from the pacing ratio thereby providing a more accurate metric of pacing efficacy and/or efficiency, which may referred to as a pacing effectiveness ratio.

A feature-based classification may enable beat-to-beat rhythm classification in a device (e.g., IMD 16) employing cardiac pacing (e.g., left ventricular fusion pacing, biventricular pacing, etc.) and may add value to the device by providing useful diagnostic indices to a physician. The computational price involved in such feature-based beat-to-beat classifications may be minimal and may be implemented within the architecture of devices such as the IMD 16 described herein with reference to FIGS. 1-3. For example, the exemplary methods described herein may combine algebraic operations and comparisons and/or may require a single normalization per beat compared to multiple intensive mathematical operations and normalizations that are often required for detailed template matching algorithms.

The exemplary methods and/or devices described herein may track, or monitor, the effectiveness of pacing therapy by analyzing one or more features of a sensed morphological waveform corresponding to a paced event for one or more monitored electrical vectors of the patient's heart. As used herein, a sensed morphological waveform may correspond to a paced event by occurring within a predetermined, or selected, time period, or sensing window, (e.g., 200 milliseconds) after the delivery of pacing stimulus. The sensed morphological waveform may, e.g., result from the delivery of pacing stimulus and/or intrinsic conduction. One manifestation of the basic flow can be seen in exemplary method 100 of FIG. 4. Exemplary method 100 includes various processes to monitor two or more electrical vectors and analyze whether each paced event is effective based on one or more features of sensed morphological waveforms within the two or more electrical vectors. Exemplary method 100 is intended to illustrate the general functional operation of the devices described herein, and should not be construed as reflective of a specific form of software or hardware necessary to practice all of the methods described herein. It is believed that the particular form of software will be determined primarily by the particular system architecture employed in the device (e.g., IMD 16) and/or system (e.g., system) and by the particular detection and therapy delivery methodologies employed by the device and/or system. Providing software and/or hardware to accomplish the described methods in the context of any modern IMD, given the disclosure herein, is within the abilities of one of skill in the art.

Figure 4:
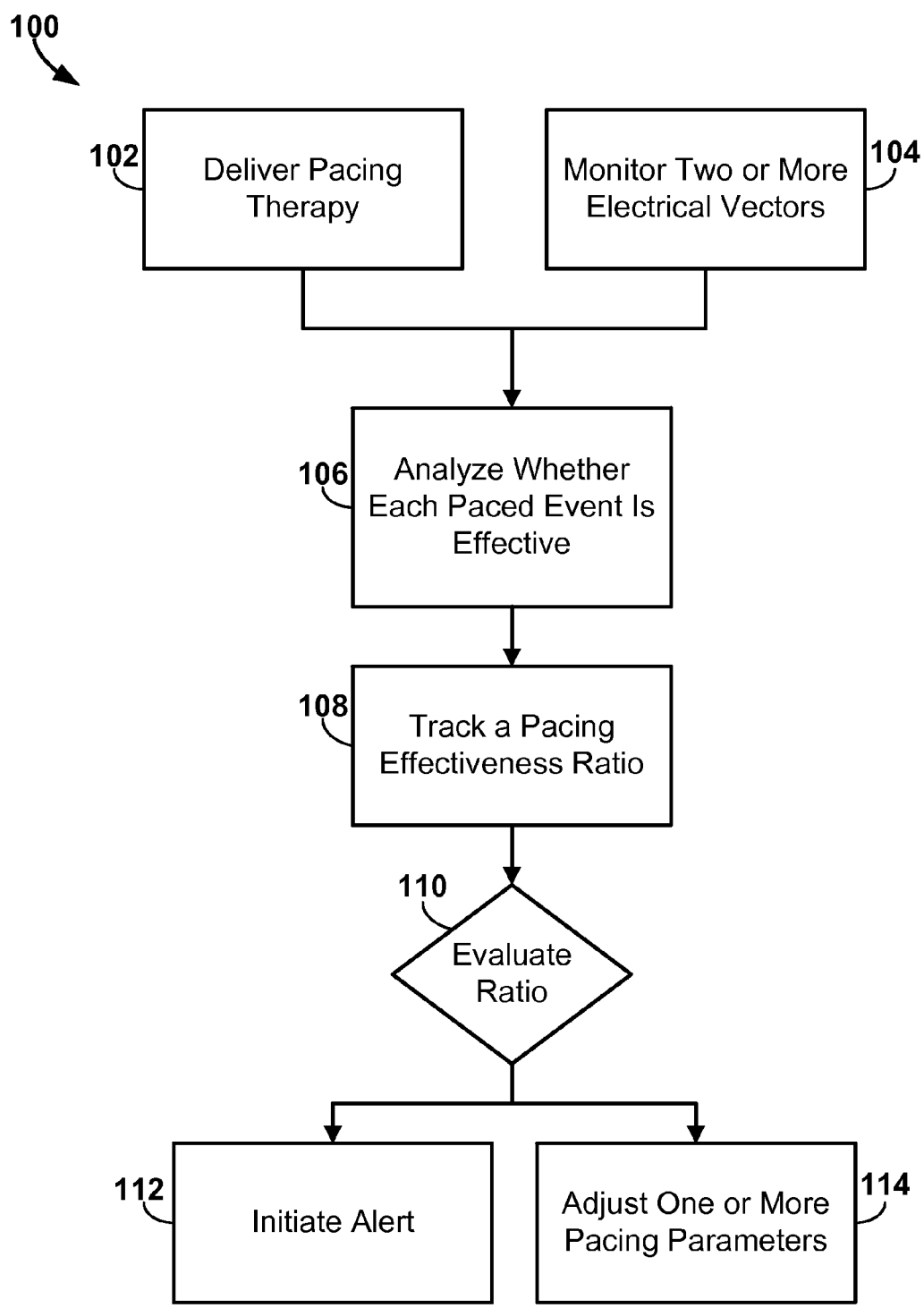
FIG. 4 is a flow chart of an exemplary method for use in tracking effectiveness of pacing therapy, e.g., using the IMDs of FIGS. 1-3.

The exemplary method 100 of FIG. 4 includes delivering pacing therapy 102 (e.g., using the IMD 16 and/or system 10 described herein). Delivering pacing therapy 102 may include monitoring a patient's heart and delivering electrical pacing pulses to the patient's heart, e.g., to maintain the patient's heart beat (e.g., to regulate a patient's heart beat, to improve and/or maintain a patient's hemodynamic efficiency, etc.)

As described herein, during the delivery of pacing therapy 102, the pacing therapy 102 may become less effective due to, e.g., lead dislodgement, exit block, extracardiac stimulation, ventricular ectopy, intrinsic rhythm interference with pacing, a change in cardiac substrate/tissue proximate the pacing electrode, changes in ventricular conduction velocity, changes in ventricular conduction patterns, changes in intrinsic AV delays, changes in heart rate, changes in sympathetic or parasympathetic stimulation, etc. Exemplary method 100 tracks the effectiveness of the pacing therapy by monitoring two or more electrical vectors 104 of the patient's heart during the delivery of pacing therapy 102 using electrodes not configured to pace the patient's heart.

Each of the two or more electrical vectors may be monitored using a pair of electrodes having at least one different electrode from each other (e.g., such that each of the two or more electrical vectors are different from one another by at least one electrode). In one or more embodiments, each pair of electrodes may share one electrode (e.g., a housing electrode of an IMD). For example, a first electrical vector may utilize an electrode proximate a patient's right ventricle (e.g., a ring electrode on a RV lead) and a housing electrode of an implantable medical device (e.g., IMD 16), and a second electrical vector may utilize electrode proximate a patient's left ventricle (e.g. a ring electrode on a LV lead) and a housing electrode of an implantable medical device (e.g., IMD 16). Further, for example, a first electrical vector may utilize an electrode proximate a patient's right ventricle (e.g., a ring electrode on a RV lead) and a housing electrode of an implantable medical device (e.g., IMD 16), and a second electrical vector may utilize electrode proximate a patient's superior vena cava (SVC) and a housing electrode of an implantable medical device (e.g., IMD 16).

Each paced event of a plurality of paced events, e.g., occurring after the delivery of pacing therapy 102 (e.g., a sensed morphological waveform may correspond to a paced event by occurring within a predetermined, or selected, time period, or sensing window, after the delivery of pacing stimulus), may be monitored by two or more electrical vectors of a patient's heart over a period of time. Further, each paced event may be analyzed to determine whether each paced event has a predetermined level of effectiveness 106. As used herein, a "predetermined level of effectiveness" may be defined as a minimal level of pacing therapy operable to effectively regulate a patient's heartbeat. In at least one embodiment, the predetermined level of effectiveness may be determined by a physician modifying various parameters and timings like atrioventricular (AV) delays, ventriculo-ventricular (VV) delays, etc. and monitoring effectiveness by measuring cardiac contractility using echocardiography. In other words, a predetermined level of effectiveness may be the floor, or minimum threshold, at which pacing therapy may continue to operate before triggering additional device action, e.g., initiate an alert, adjusting one more pacing parameters, initiating one or more capture management processes, etc.

For example, if a proportion of optimal beats fall below a certain threshold, an alarm may be triggered including an audible beep or a CARELINK transmission may be triggered to raise a flag indicating urgent evaluation of the patient for possible loss of optimal pacing. In at least one embodiment, the threshold may have a nominal value of 90%. Further, the threshold may be a value programmable by a physician specific to a patient. If a proportion of paced beats that resemble intrinsic activation increases beyond a certain threshold, then an exemplary device may perform a number of steps before triggering a similar alarm such as, e.g., pace at a shorter A-V delay and evaluate if the proportion of optimal pacing increases above the threshold. If a proportion of optimal pacing does not increase, the exemplary device may evoke a pace capture management routine in which the device attempts, or tries, to increase the LV and/or RV pacing outputs in an effort to re-obtain capture and/or effective pacing.

To analyze whether each paced event is effective based on the monitored electrical vectors 106, the exemplary method 100 may analyze at least one feature (e.g. one or more features) of a sensed morphological waveform (e.g., corresponding to each paced event such as occurring within a predetermined, or selected, time period, or sensing window, (e.g., 200 milliseconds) after the delivery of pacing stimulus) within each electrical vector of the two or more monitored electrical vectors. In at least one embodiment, the exemplary method 100 may analyze at least two features of the sensed morphological waveform of, or for, each electrical vector. Exemplary features may include minimum values, maximum values, minimum slopes, maximum slopes, peak-to-peak amplitude, maximum value timings, minimum value timings, a peak number based on the ratio of the positive peak/maximum value and the negative peak/minimum vale, timing between RV and LV electrogram fiducial points, relative values and timing within a pre-defined windows, etc.

By monitoring and analyzing two or more electrical vectors, pacing events may be confirmed as effective or ineffective by using more than one vector. In other words, one vector including a morphological waveform indicating effective pacing therapy for a paced event may confirm another vector including a morphological waveform indicating effective pacing therapy for the same paced event. In essence, the two vectors may be used to confirm one another. In at least one embodiment, a paced event may be determined to be effective if all of the two or more monitored electrical vectors include morphological events that have features that are indicative of effective pacing therapy (e.g., a predetermined level of effectiveness). In at least another embodiment, a paced event may be determined to be effective if a selected number (e.g., one, two, etc.) of the two or more monitored electrical vectors include morphological events that have features that are indicative of effective pacing therapy (e.g., a predetermined level of effectiveness).

Exemplary methods and/or processes for analyzing whether a paced event is effective 106 based on at least one feature of a morphological waveform of two or more monitored vectors are described herein with reference to FIGS. 7-14.

Delivering pacing therapy 102, monitoring two or more electrical vectors 104, and analyzing whether each paced event is effective 106 may occur over a period of time measured in, e.g., paces, heart beats, hours, days, months, etc. Over such period of time, a pacing effectiveness may be tracked 108. Pacing effectiveness may be tracked by storing, or recording, an amount of effectively paced heart beats, an amount of intrinsic, un-paced heart beats, an amount of ineffective heart beats, an amount of fusion events, an amount of pseudo-fusion events, an amount of unknown events, etc. As used herein, a fusion event may be defined as a paced event in which intrinsic ventricular activation (e.g., ventricular activation from intrinsic conduction) fuses, or merges, with paced ventricular activation (e.g., ventricular activation due to pacing stimulus), and as such, is less effective than a fully paced, or effectively paced, event. As used herein, a pseudo-fusion event may be defined as a paced event in which paced ventricular stimulus is delivered after the ventricle has already depolarized due to intrinsic ventricular activation, and as such, is ineffective.

For example, pacing effectiveness may be tracked, or monitored using a pacing effectiveness ratio, which is a ratio between an amount of paced events over time having a predetermined level of effectiveness (e.g., effectively paced beats) and an amount of paced events. Since the pacing effectiveness ratio actually provides a metric by which pacing effectiveness may be monitored, it may be described that it provides more resolution than a traditional LV or BV pacing ratio, which is merely the number of paced heart beats divided by the total number of heart beats. In other words, instead of only keeping track of how many beats were paced as with a traditional pacing ratio, the pacing effectiveness ratio provides more detail with respect to the pacing therapy being delivered (e.g., broadly, whether the pacing therapy being delivered was actually effective). For example, the proportion of paced beats that were effective may be calculated by discounting all the fusion, pseudo-fusion, and unknown events.

Further, pacing effectiveness may change over the course of a time period due to, e.g., physical activity of the patient, etc. As such, the pacing effectiveness ratio may be tracked over a time period such that pacing therapy may be evaluated for different portions of the time period. For example, a clinician may be able to view the pacing effectiveness of pacing therapy for a patient over the course of a day.

Figure 15A:
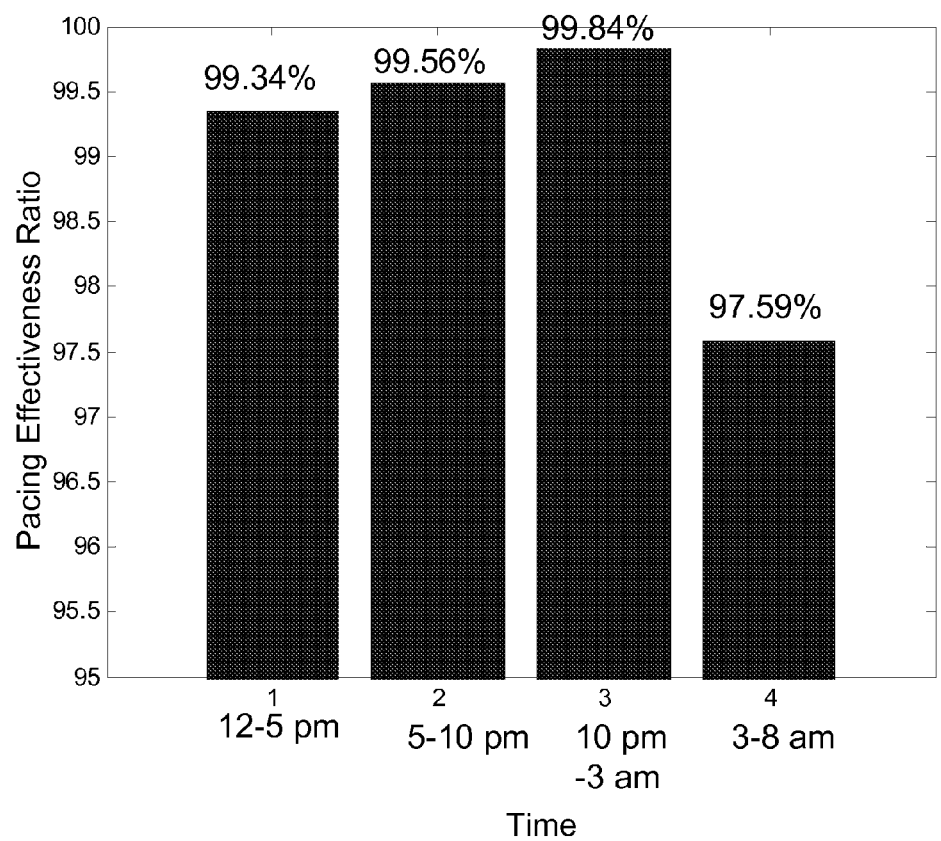
FIGS. 15A-B are graphs of pacing effectiveness ratio over time for patients.
Figure 15B:
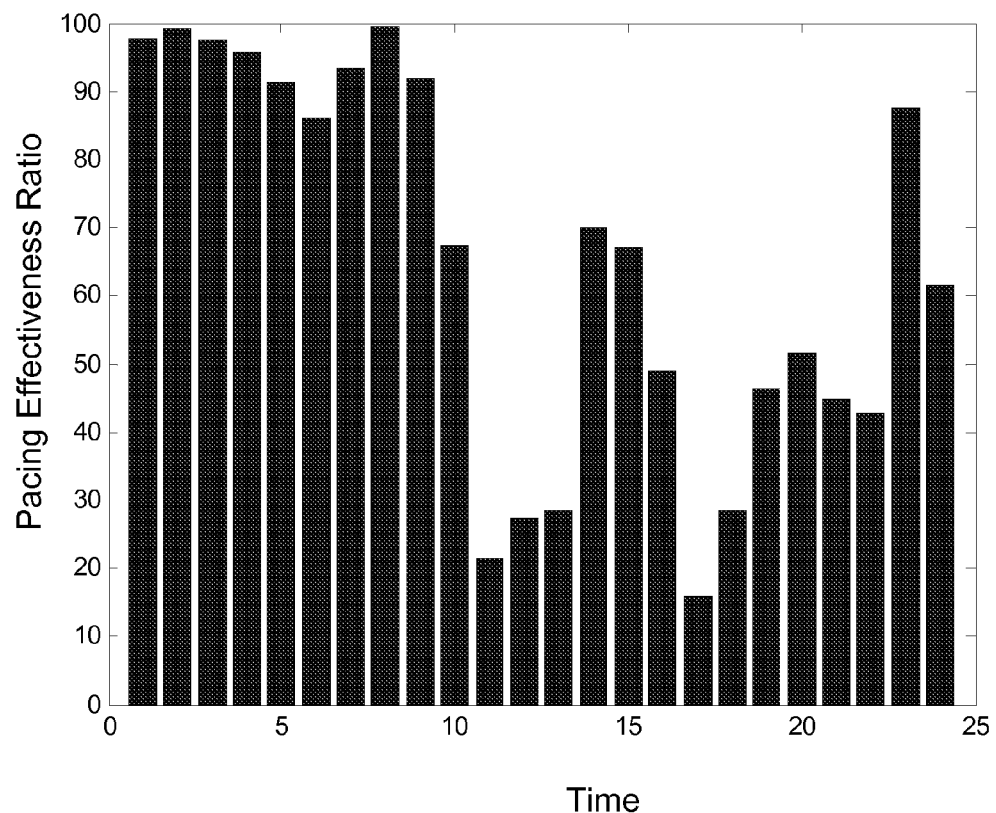

Exemplary graphs depicting pacing effectiveness ratios monitored over time are shown in FIGS. 15A-B. As shown in FIG. 15A, a pacing effectiveness ratio for a patient may be 99.34% from 12:00 PM to 5:00 PM, 99.56% from 5:00 PM to 10:00 PM, 99.84% from 10:00 PM to 2:00 AM, and 97.59% from 3:00 AM to 8:00 AM. As such, pacing therapy delivered to this patient may be determined to be more effective from 12:00 PM to 3:00 AM than from 3:00 AM to 8:00 AM. In view thereof, an exemplary device providing pacing therapy (e.g., IMD 16) may change one or more pacing parameters between 3:00 AM and 8:00 AM, may initiate an alert such that the patient may see a clinician, etc. Further, for example, a clinician may view this data when evaluating the patient's pacing therapy and may adjust one or more parameters of the pacing therapy, e.g., to be delivered between 3:00 AM and 8:00 AM.

Pacing effectiveness for another patient having a predominate rhythm of chronic atrial fibrillation and atrial flutter being treated using biventricular pacing is depicted in FIG. 15B. As shown, the pacing effectiveness is relatively high (e.g., 85% or higher) for hours 0 through 9 but then decreases significantly reaching low points at hours 11-13 and 17-18.

Intermittently, or periodically, the pacing effectiveness ratio may be evaluated 110 to, e.g., determine if any of one or more actions should be taken. The pacing effectiveness ratio may be compared to a nominal threshold value such as, e.g., 90%. If the pacing ratio decreases below the threshold value, then one or more actions may be triggered. Further, the pacing effectiveness ratio may only temporarily decrease below, or be less than, the threshold value. As such, the evaluation process 110 may allow that the pacing effectiveness ratio to be below the threshold value for a selected period of time (e.g., 6 hours, etc.). In at least one embodiment, it may be determined that one or more actions may be taken if the effective pacing ratio consistently remains below 90% when monitored at two different times of the day.

If the pacing effectiveness ratio is evaluated 110 and it is determined that one or more actions should be taken, the exemplary method 100 may initiate an alert, or alarm, 112 to indicate to the patient or a technician that pacing therapy may be ineffective (e.g., an alert may include a warning sound or other perceptible signal that indicates to the patient that the patient should visit a physician for further investigation such as checking for lead dislodgement, modification of rate control through medication/ablation of ectopy/atrioventricular node/junction). Further, for example, as shown in FIG. 4, if the pacing effectiveness ratio is evaluated 110 and it is determined that one or more actions should be taken, the exemplary method 100 may adjust one or more pacing parameters 114 such as, e.g., pulse width, voltage, AV delay (e.g., shorten AV delay), VV delay, pacing location and/or vector, additional pacing, etc.

In at least one embodiment, exemplary method 100 may be triggered regularly or periodically over a period time (e.g., periodically throughout a day) to evaluate morphological consistency to determine whether the pacing therapy is effective (e.g., if each paced event has a predetermined effectiveness). In at least another embodiment, exemplary method 100 may operate on a beat-to-beat basis monitoring every paced event for a patient.

To analyze whether each paced event of the plurality of paced events has a predetermined level of effectiveness based on at least one feature of the sensed morphological waveform for each electrical vector of the two or more monitored electrical vectors, exemplary methods and devices described herein may compare the sensed features to one or more baseline values or reference features that are indicative of effective pacing therapy, a predetermined level of effectiveness, non-optimal pacing, ineffective pacing, fusion events, pseudo-fusion events, etc. To obtain baseline or reference features for each vector (and for each type of therapy), exemplary methods and devices described herein may collect and store one or more features of morphological waveforms for each electrical vector for each different type, or classification, of known paced events.

For example, reference features for various events such as, e.g., a fully paced or effective event, may be collected by biventricular pacing at a short A-V delay, or optimal AV or VV delays, determined by any number of existing methods (e.g., based on measurement of cardiac contractility derived from clinical imaging modalities like echocardiograms or a combination of electrocardiograms and intracardiac electrograms). Further, paced events may be classified as a fully paced, or effective, event, a fusion event, a pseudo-fusion event, or an unknown event. As such, before implementing exemplary method 100 to track effectiveness of pacing therapy, exemplary methods and devices may collect and record one or more features of the morphological waveform for each of a known fully paced, or effective, event, a fusion event, or a pseudo-fusion event. For example, various pacing parameters may be adjusted such as, e.g., AV delay and VV delay, to provide various paced events such as effectively paced events, fusion events, etc. and reference features may be measured by monitoring one or more vectors during the such paced events. Such collected and recorded features may then be used by exemplary methods, e.g., such as exemplary method 100, to determine, or analyze, whether each paced event of the plurality of paced events has a predetermined level of effectiveness.

Figure 5:
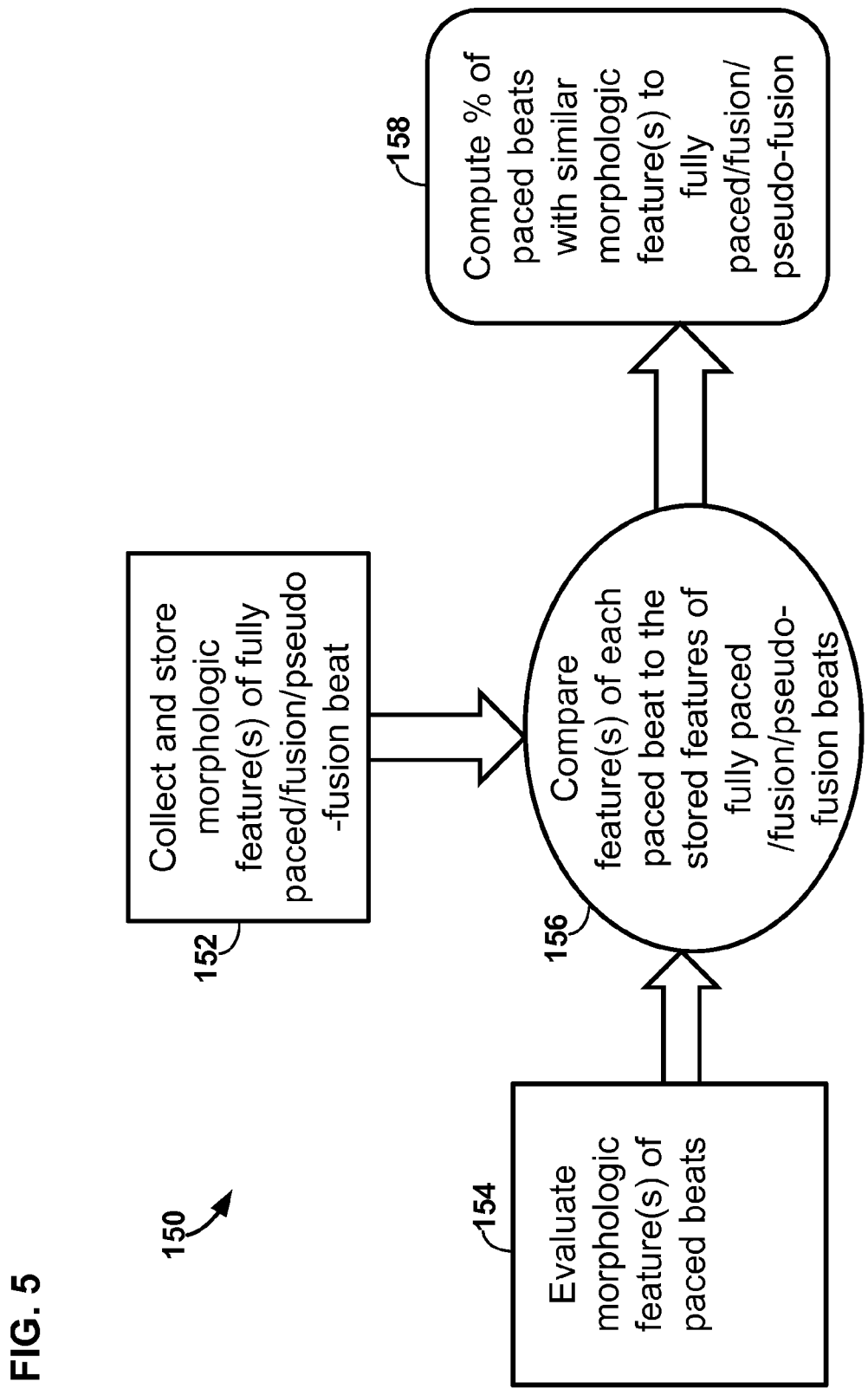
FIG. 5 is a flowchart of an exemplary method for use in obtaining one or more morphological features and in evaluating one or more morphological features for use in tracking effectiveness of pacing therapy.

Exemplary method 150 for use in obtaining one or more morphological features and in evaluating one or more morphological features for use in tracking effectiveness of pacing therapy is depicted in FIG. 5. Method 150 may include collecting and storing morphological features of fully paced events, fusion events, pseudo-fusion events, and subsequently, input, or feed, these morphological features for each of the events into a comparison algorithm 156, which may be later used as reference information to analyze one more features of sensed morphological waveforms during pacing to determine pacing effectiveness (e.g., whether each paced event has a predetermined level of effectiveness). An exemplary method for use in obtaining one or more morphological features will be described further herein with reference to FIG. 6.

Similar to exemplary method 100, exemplary method 150 may evaluate morphological features of paced beats 154 continually or periodically over a period of time and compare those features of each paced beat to the stored features of a fully paced event, a fusion event, and a pseudo-fusion event 156. From the comparison 156, exemplary method 150 may compute percentages of paced beats with similar morphological features to each of a fully paced event, a fusion event, and a pseudo-fusion event 158. Such percentages may be used for initiating one or more actions or may be used for diagnostic purposes, e.g., by a clinician.

Multiple features on multiple vectors (e.g., far-field vectors) may be monitored and analyzed to determine pacing effectiveness because multiple features from multiple vectors may characterize a given pattern of activation (e.g., effective or ineffective) more accurately than, e.g., one or more features on a single vector (e.g., two different kinds of activation may produce the same kind of morphology at a single EGM vector). Hence, sensing and analyzing a plurality of features for a plurality of vectors may be more effective in tracking deviations from a given optimal activation. Also, far-field vectors may be selected as opposed to near-field vectors because, e.g., far-field vectors may offer a more global view of electrical activation.

Figure 6:
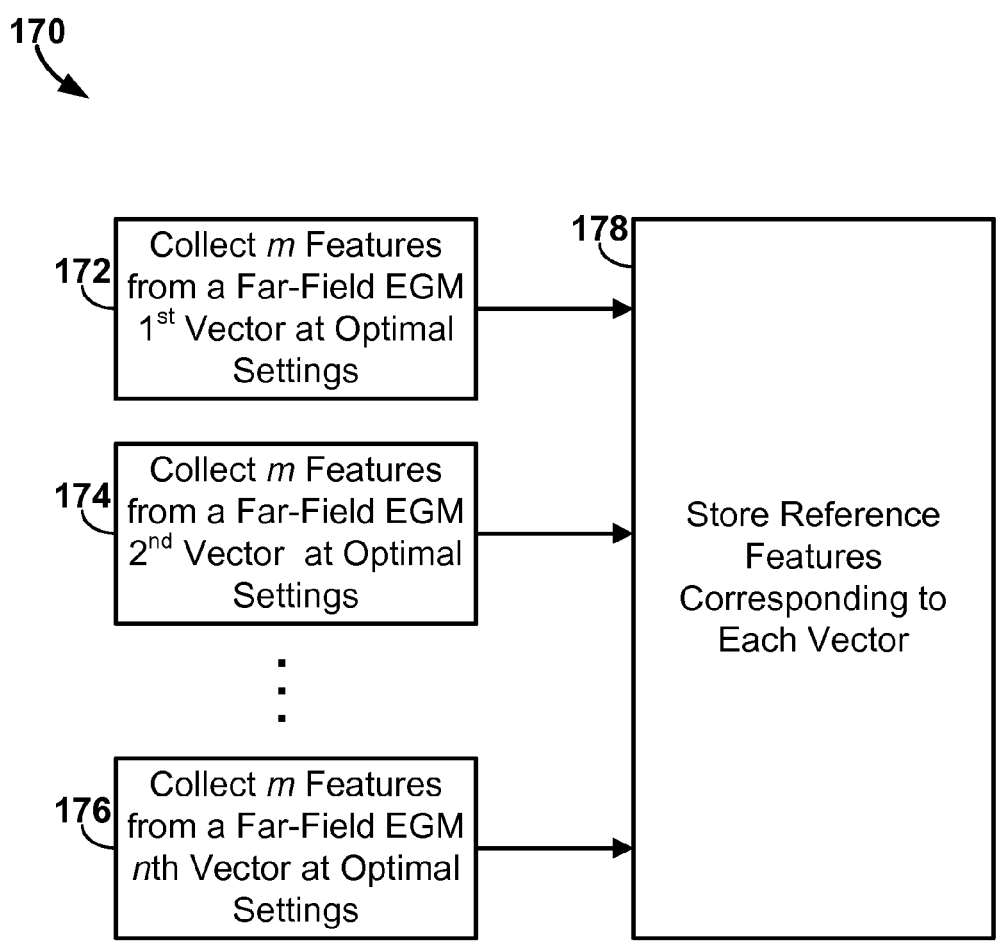
FIG. 6 is a flowchart of an exemplary method for use in obtaining one morphological features.

Exemplary method 170 of FIG. 6 depicts collecting and storing of multiple features from multiple far-field electrogram signals of multiple vectors at optimal settings. For example, method 170 may collect m features from a far-field electrogram of a first vector at known optimal settings 172, m features from a far-field electrogram of a second vector at known optimal settings 174, and may collect m features from far-field electrogram of a nth vector at known optimal settings 176. Although exemplary method 170 collects one or more features at known optimal settings (e.g., known optimal settings that deliver effective pacing therapy to yield effective pacing events, or events having a predetermined level of effectiveness), other exemplary methods may collect and store features of non-optimal paced events such as, e.g., fusion events, pseudo-fusion events, etc.

After each feature of m features from each vector (e.g., n vectors) have been collected at optimal settings, the features may be stored as reference features corresponding to each vector 178. These stored reference features may be used to analyze whether paced events are effective at a later time, e.g., as shown by process 106 of FIG. 4 and process 156 of FIG. 5.

The variables m and n represent a plurality, or two or more. In other words, a plurality of features from each of the plurality of vectors may be collected for each of a plurality of events, and each of the plurality features for each of the plurality vectors for each of the plurality of events may be stored as reference features corresponding to each vector to be used later to evaluate pacing effectiveness. In at least one embodiment, at least two features from each of two electrical vectors may be collected and stored (e.g., as reference features corresponding to a particular vector) to be used later in the evaluation of pacing effectiveness.

As described herein, multiple electrical vectors may be used, e.g., monitored and evaluated, to determine whether each paced event of a plurality of paced events has a predetermined level of effectiveness. Since each of the multiple electrical vectors is different from one another, each vector may have different morphological features for each paced event than any other vector. Thus, the metrics used to analyze the morphological waveform for each different vector may be different from vector to vector.

Figure 7:
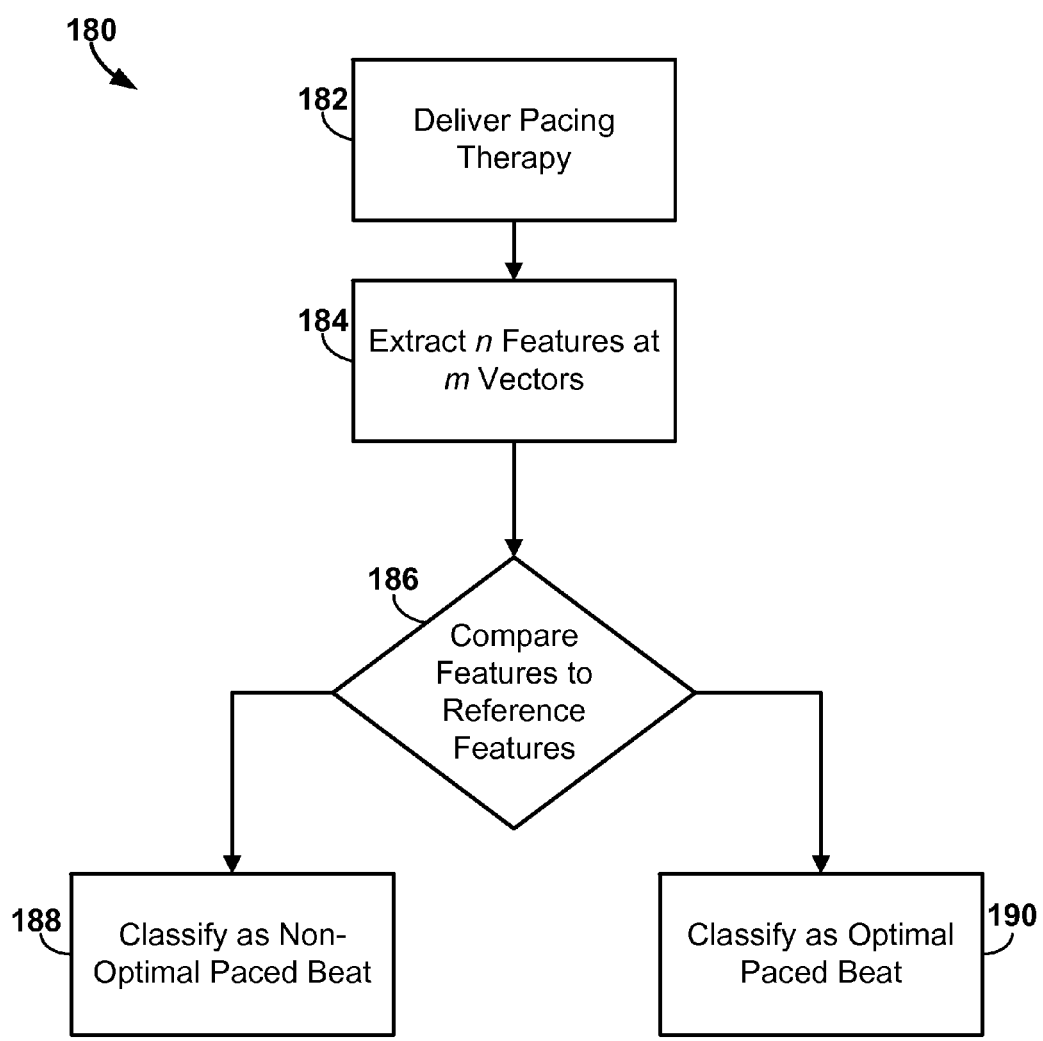
FIG. 7 is a flowchart of an exemplary method for use in analyzing pacing effectiveness based on one or more morphological features.

An exemplary method 180 for use in determining pacing effectiveness using one or more morphological features is depicted in FIG. 7. Similar to delivering pacing therapy 102 of exemplary method 100 described herein with reference to FIG. 4, exemplary method 180 includes delivering pacing therapy 182. During the delivery of pacing therapy 182, the exemplary method 180 may extract n, or a plurality of, features at, or from, m, or a plurality of, vectors. Exemplary method 180 may then compare the extracted or sensed features of the vectors to the reference features collected and stored previously, e.g., using exemplary method 170. Through this comparison 186, each of the paced events may be classified either as a non-optimal paced beat 188 (e.g., a fusion event, a pseudo-fusion event, an unknown, ineffective event, etc.) or as an optimal paced beat 190 (e.g., a fully paced event, an effectively paced heart beat, a paced event having a predetermined level of effectiveness, etc.).

Figure 8A:
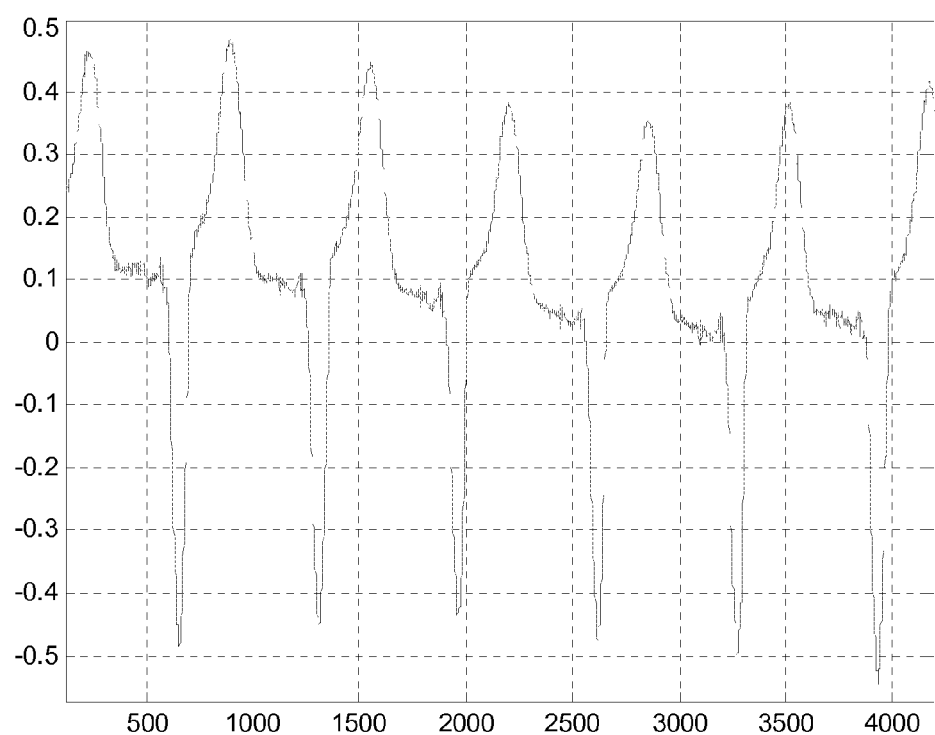
FIGS. 8A-8C are graphs of far-field right ventricular electrograms for different cardiac rhythms.
Figure 8B:
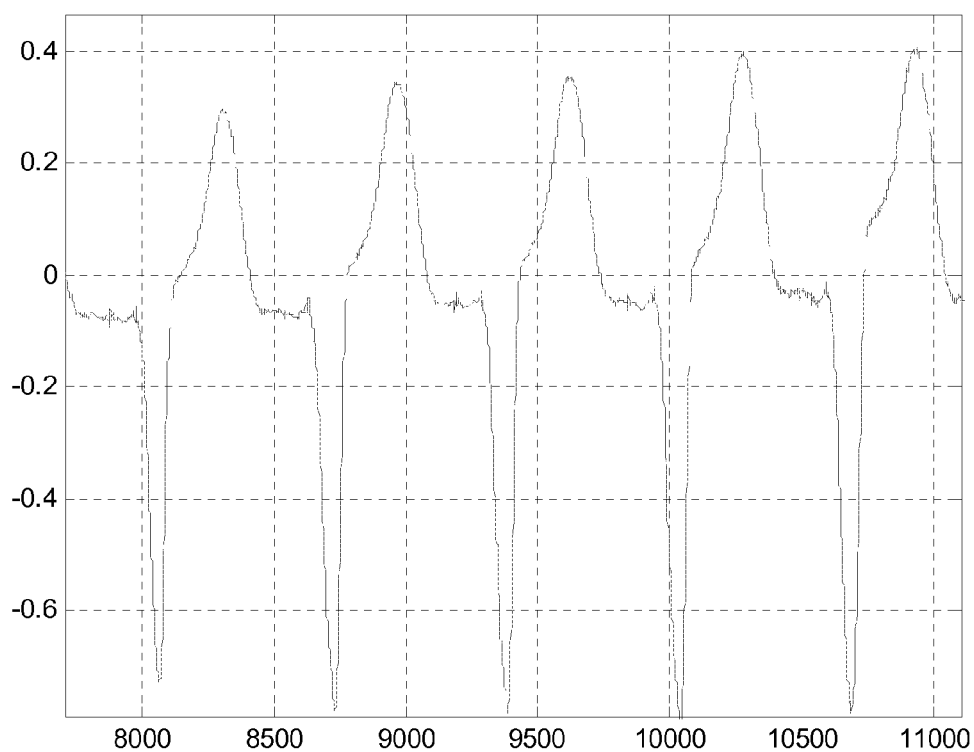
Figure 8C:
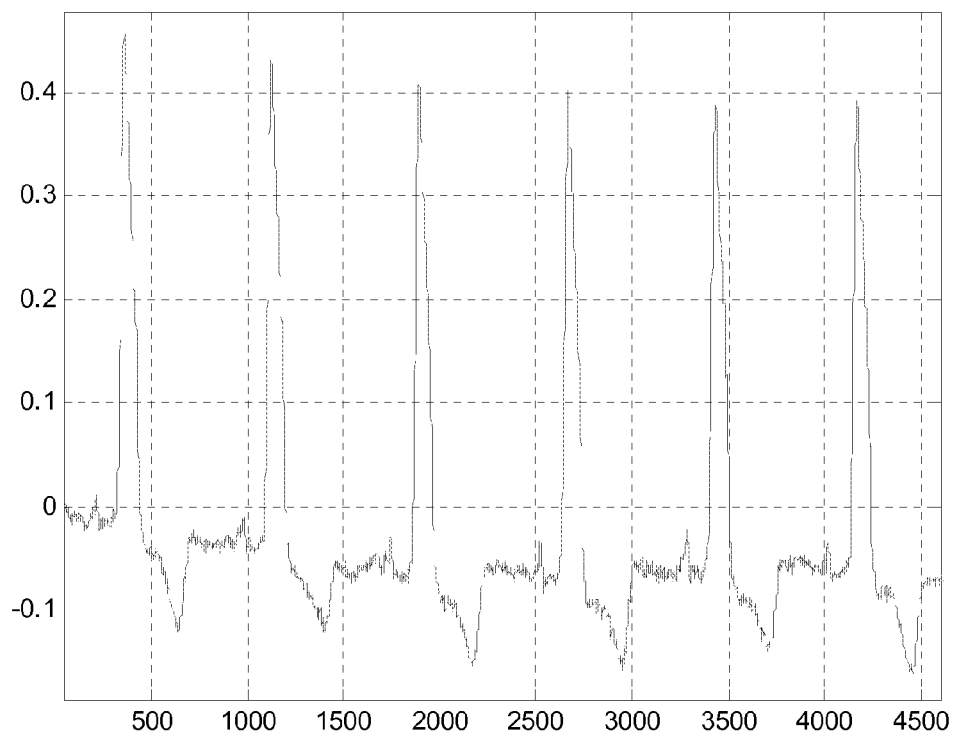

Far-field right ventricular electrograms monitored using a RV coil electrode to housing electrode vector or an SVC electrode to housing electrode vector for different cardiac rhythms are depicted in FIGS. 8A-C. Such far-field right ventricular electrograms may be used to collect and store one or more reference features from morphological waveforms of an electrogram (e.g., at a vector) that may be used to analyze whether a paced event has a predetermined level effectiveness. Generally, data gathered from the electrograms of FIGS. 8A-C may provide a beat-to-beat rhythm classification scheme (e.g., feature-based discrimination for far-field RV electrograms, far-field LV electrograms, and/or device leadless electrocardiograms) for discerning evoked responses to biventricular pacing, left ventricular pacing, right ventricular pacing, and intrinsic conduction (natural sinus rhythm).

The electrogram of FIG. 8A depicts rhythm type 1 that corresponds to biventricular pacing, the electrogram of FIG. 8B depicts rhythm type 2 that corresponds to left ventricular pacing, and the electrogram of FIG. 8C depicts rhythm type 3 that corresponds to natural sinus rhythm, or intrinsic conduction. In this example, the features that may be collected and stored, and subsequently used to analyze a morphological waveform to determine whether the paved event was effective, may be normalized peak-to-peak amplitude and peak number. Peak number is a number based on the ratio of the positive peak and the negative peak.

Each of the electrograms of FIGS. 8A-C was averaged over five beats to provide reference features. The electrogram of FIG. 8A provided a normalized peak-to-peak amplitude of 1.18 and a peak number of −1. The electrogram of FIG. 8B provided a normalized peak-to-peak amplitude of 0.82 and a peak number of −1. The electrogram of FIG. 8C provided a normalized peak-to-peak amplitude of 1.13 and a peak number of +1. Such reference features may be used in determining pacing effectiveness.

Figure 9:
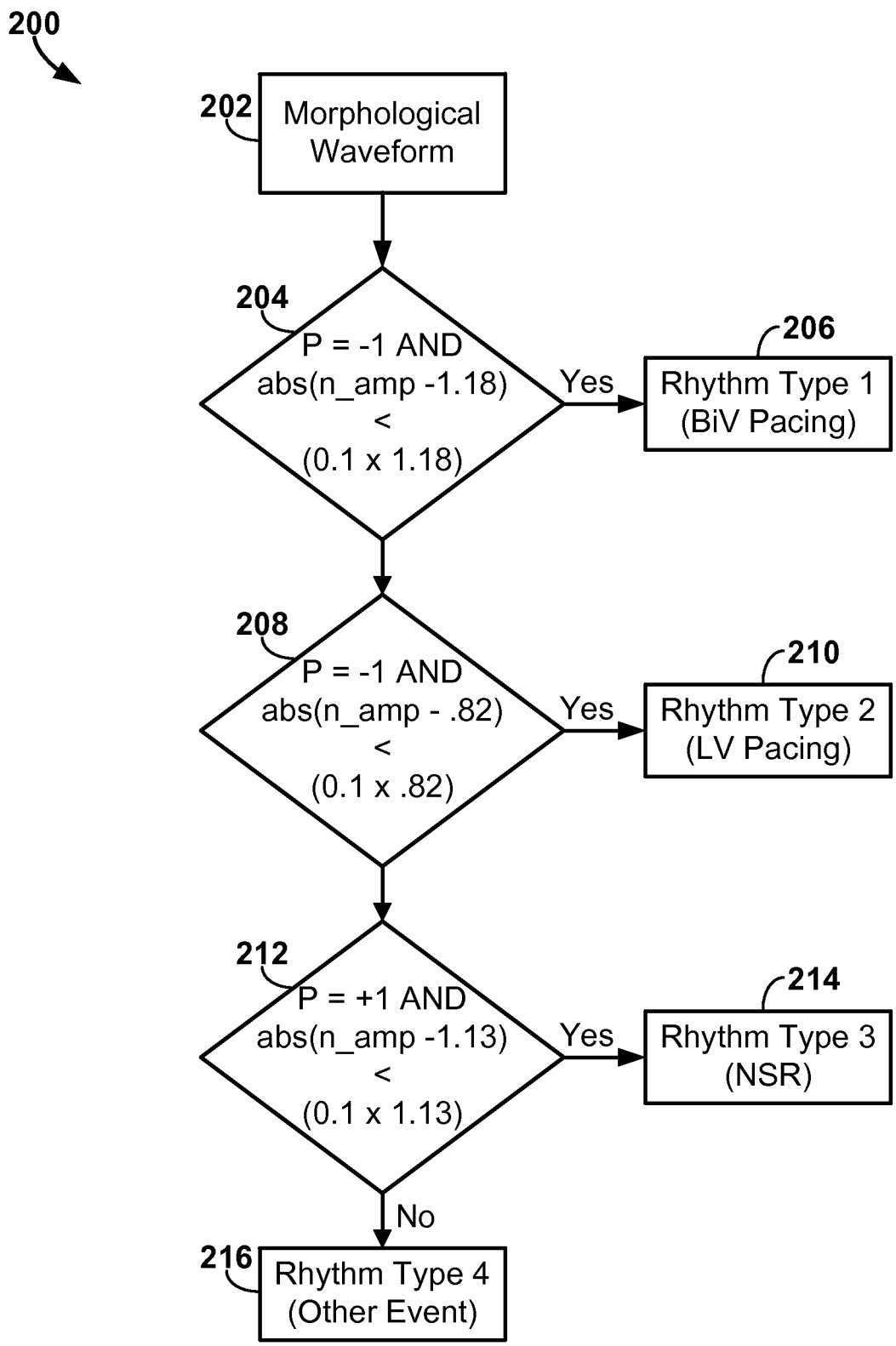
FIG. 9 is a flowchart of an exemplary method for use in classifying morphological waveforms using features such as peak-to-peak amplitude and peak number.

An exemplary method 200 using the reference features derived, or extracted, from the electrograms of FIGS. 8A-8C is shown in FIG. 9. At the outset, a vector of the patient's heart is monitored (e.g., the same vector used for the collection and storage of reference features from the electrograms of FIGS. 8A-8C) during pacing therapy for a paced event and a morphological waveform corresponding to a paced event (e.g., corresponding to a paced event such as occurring within a predetermined, or selected, time period, or sensing window, after the delivery of pacing stimulus) is extracted therefrom. The normalized peak-to-peak amplitude and the peak number of the morphological waveform of the vector resulting from the monitored vector may be provided 202. If the peak number equals −1 and the absolute value of the normalized peak-to-peak amplitude is within 10% of 1.18 204, then the morphological waveform may be classified as rhythm type 1, which corresponds to biventricular pacing. If the peak number equals −1 and absolute value of the normalized peak-to-peak amplitude is within 10% of 0.82, then the morphological waveform may be classified as rhythm type 2, which corresponds to left ventricular pacing. If the peak number equals +1 and the absolute value of the peak-to-peak amplitude is within 10% of 1.13, then the morphological waveform may be classified as rhythm type 3, which corresponds to natural sinus rhythm or an intrinsic conduction.

If the peak number and the absolute value of the peak to peak amplitude do not meet the conditions 204, 208, 212, then the morphological waveform may be classified as rhythm type 4, which correspond to unknown events. As a result, the peak number and the absolute value of the peak-to-peak amplitude may be used to determine whether the sensed morphological waveform representative of the paced event indicates biventricular pacing, left ventricular pacing, natural sinus rhythm, or an unknown event. Such results may be used to determine whether the paced event has a predetermined level effectiveness. For example, if biventricular pacing is being delivered to the patient and left ventricular pacing is indicated or determined using the sensed morphological waveform, then the pacing therapy delivered to the patient (BV pacing) may not be effective. Further, for example, if left ventricular pacing is being delivered to the patient and natural sinus rhythm is indicated or determined from the sensed morphological waveform, then the pacing therapy delivered to the patient (LV pacing) may not be effective. Still further, for example, if any type of pacing is being delivered to the patient and rhythm type 4, which corresponds to an unknown event, is determined, then the pacing therapy delivered the patient may not be effective. Conversely, for example, if left ventricular pacing is being delivered to the patient and rhythm type 2, which corresponds to left ventricular pacing, is determined, then the pacing therapy delivered the patient may be determined, or indicated, to be effective.

Figure 10A:
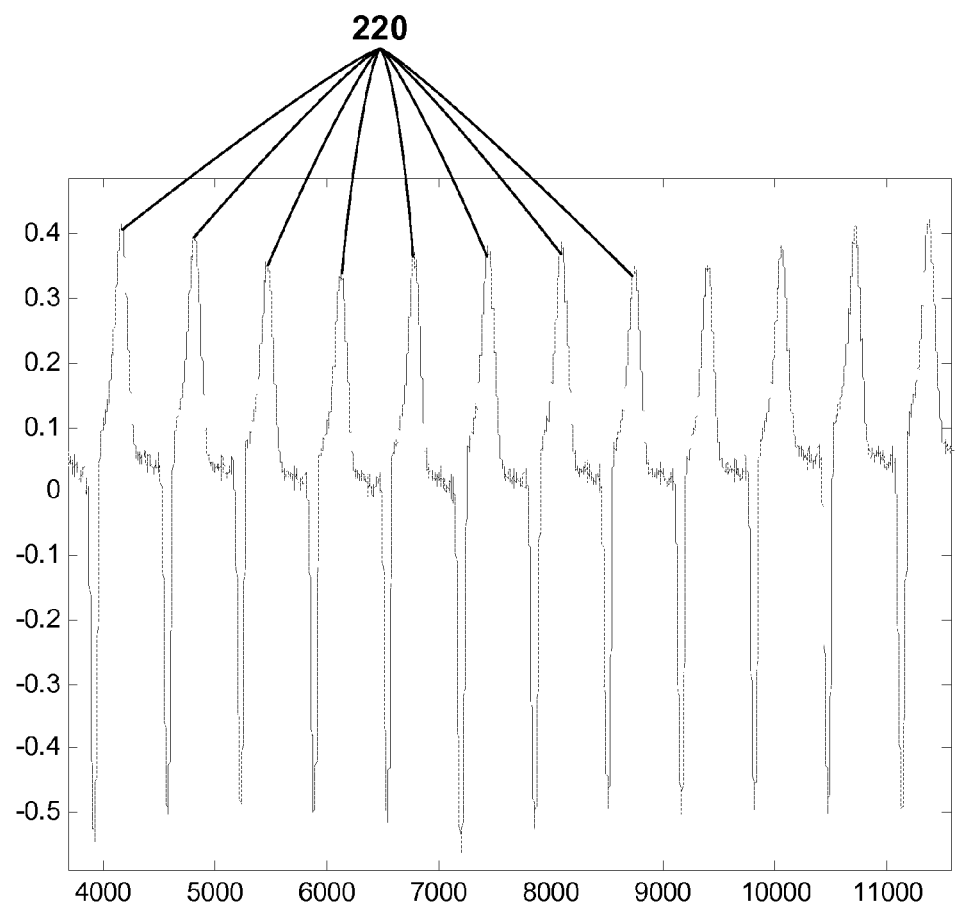
FIGS. 10A-10O are graphs of a far-field right ventricular electrograms for different cardiac rhythms.
Figure 10B:
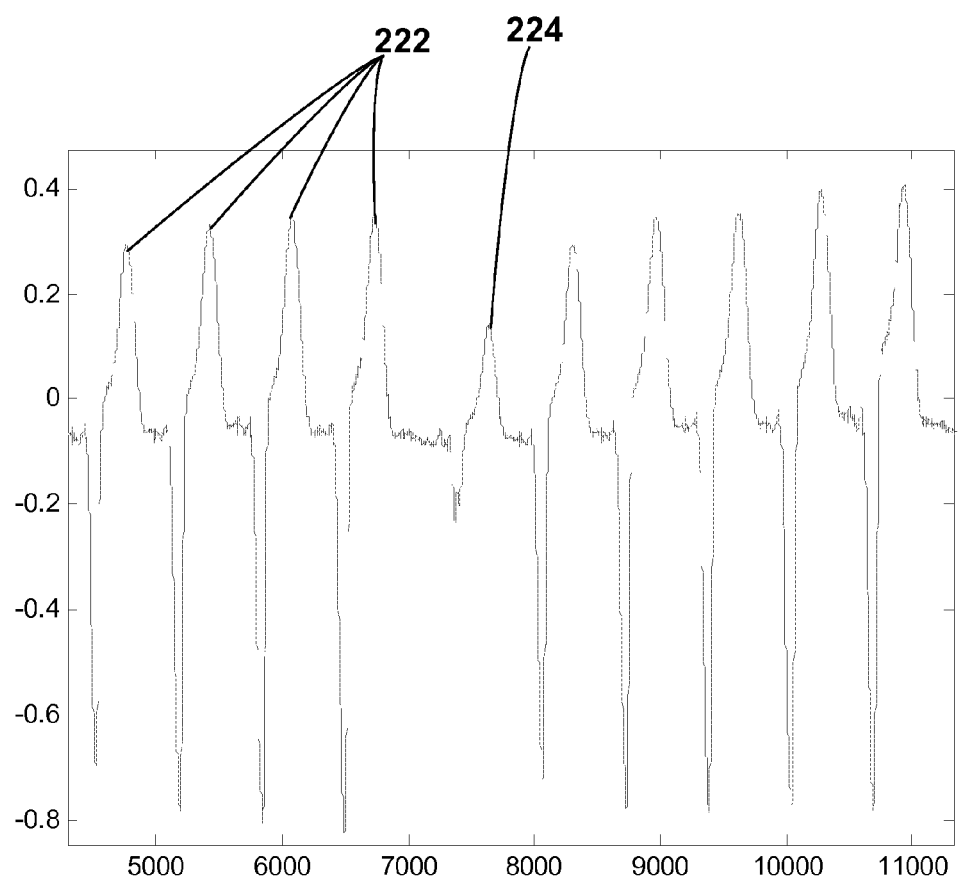
Figure 10C:
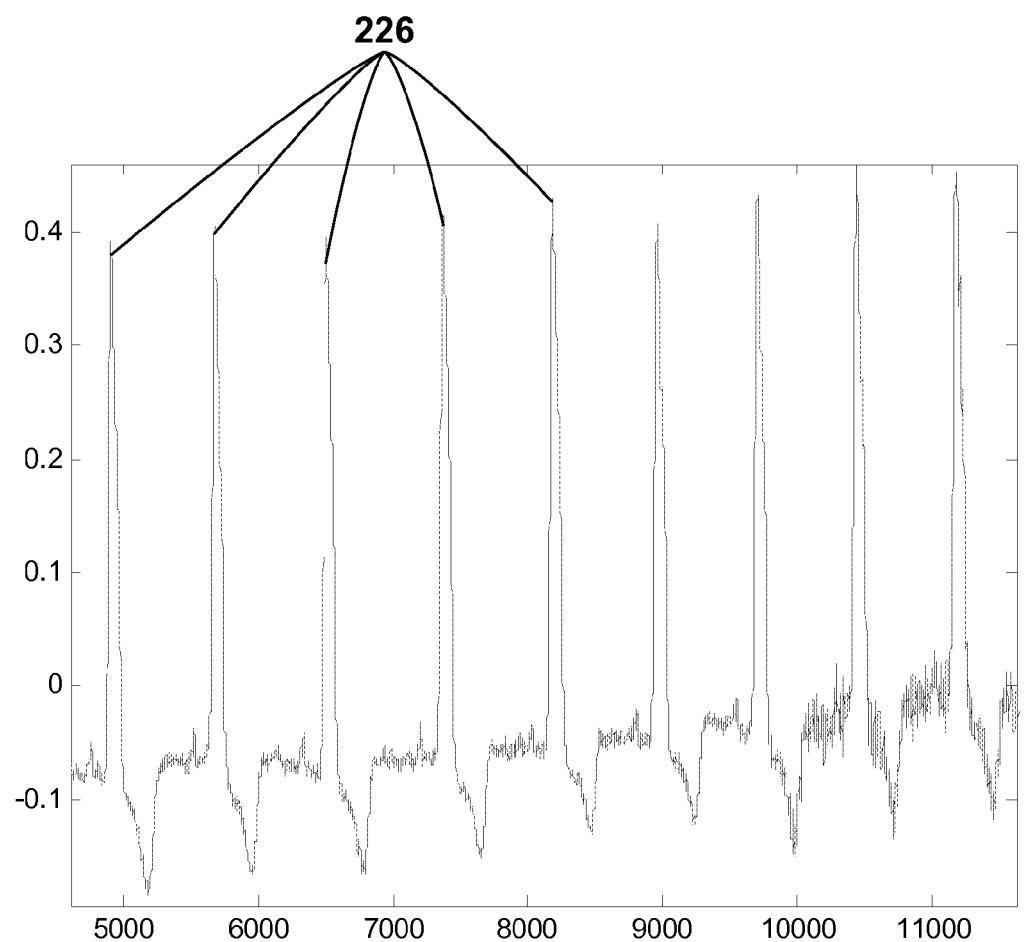

Graphs of far-field right ventricular electrograms for different cardiac rhythms classified using the exemplary method of FIG. 9 are shown in FIGS. 10A-10C. A ventricular electrogram for biventricular pacing is shown in FIG. 10A. Using the exemplary method of FIG. 9, each of the paced events 220 shown in FIG. 10A were classified as type 1, which corresponds to biventricular pacing. In other words, each of the paced events 220 has a predetermined level of effectiveness.

A ventricular electrogram for left ventricular only pacing is shown in FIG. 10B. Using the exemplary method of FIG. 9, all but one of the paced events 222 shown in FIG. 10B were classified as type 2, which corresponds to left ventricular only pacing. The extraordinary paced event 224 was classified as an unknown event, e.g., which may correspond to an ineffective, or non-optimal, paced event. In essence, all but one of the paced events shown in the electrogram of FIG. 10B have a predetermined level of effectiveness.

A ventricular electrogram for natural sinus rhythm is shown in FIG. 10C. Using the exemplary method of FIG. 9, each of the events 226 shown in FIG. 10C were classified as type 3, which corresponds to natural sinus rhythm or intrinsic conduction. If pacing therapy is being delivered, then it may be determined that each of the paced events does not have a predetermined level of effectiveness.

As a result, the exemplary method of FIG. 9 may be used to classify an event seen in a morphological waveform of a far-field electrogram, and such classification may be used to determine whether each paced event of a plurality of paced events has a predetermined level of effectiveness. In other words, the exemplary method of FIG. 9 may be used to classify an event as an effectively paced event.

In at least one embodiment of a classification system, one of the following peak numbers +1, −1, ±0.5, ±0.375, and ±0.25 may be assigned to each beat based on the following. If the absolute value of the maximum value is greater than five times the absolute value of the minimum value, then the peak number equals +1. If the absolute value of the minimum value is greater than five times the absolute value of the maximum value, then the peak number equals −1. If the maximum value occurs before the minimum value and absolute value of the maximum value is greater than 1.2 times the absolute value of the minimum value, then the peak number equals +0.25. If the maximum value occurs before the minimum value and absolute value of the minimum value is greater than 1.2 times the absolute value of the maximum value, then the peak number equals +0.375. If the minimum value occurs before the maximum value and absolute value of the maximum value is greater than 1.2 times the absolute value of the minimum value, then the peak number equals −0.25. If the minimum value occurs before the maximum value and absolute value of the minimum value is greater than 1.2 times the absolute value of the maximum value, then the peak number equals −0.375. If none of these conditions are met, then the peak number equals −0.5.

The normalized peak-to-peak amplitude (n_amp) is the maximum value minus the minimum value divided by the greater of the absolute value of the maximum and minimum values.

The peak number in the normalized peak to peak amplitude may be sequentially compared to stored features of morphological waveforms in EGM collected during fusion pacing (p1, n_amp1), biventricular pacing (p2, n_amp2), and intrinsic rhythm (p3, n_amp3). For classification into any one of the above categories, the peak number (p) of the current beat must equal the peak number of that category and the absolute difference in peak-to-peak normalized amplitude must be less than a certain percentage (10%) of the normalized amplitude of that category. If a beat could not be classified into any one of the above categories, it may be classified as other or unknown event (e.g., oversensing, premature beat, etc.). In one or more embodiments, the reference features may be updated periodically to reflect any changes that might occur in these rhythms over time.

In at least one embodiment, the exemplary methods for tracking effectiveness may include deriving multiple reference features from electrograms at a plurality of vectors for an optimal device setting (e.g., which produces a desired kind of activation considered beneficial for the patient), which may be auto-programmed by the device itself or manually by a clinician based on any number of methods, and for intrinsic activation (e.g., when pacing is turned off). The exemplary methods and devices described herein may further include determining if each paced beat is optimal or non-optimal, or have a predetermined effectiveness or not, depending on a comparison of those same features at the same vectors. Further, the exemplary methods and devices may keep track of optimal paced beats and may maintain a counter of the number of paced beats that resemble intrinsic activation.

A broad morphologic descriptor (BMD), which quantitatively describes the basic shape of waveform morphology, using multiple features may be used to analyze whether each paced event has a predetermined level of effectiveness. For example, the BMD may utilize one or more of the following features: an absolute value of the maximum value of a morphological waveform, absolute value of the minimum value of a morphological waveform, and max time value representing when the maximum value occurs in a morphological waveform, min time value representing when the minimum value occurs in a morphological waveform, a ratio (r) of the maximum to the minimum amplitude of a morphological waveform, a maximum slope (MaxS) of a morphological waveform, minimum slope (MinS) of a morphological waveform, number of peaks (np) of a morphological waveform (e.g., the number of times the slope changes sign from +ve to −ve), number of nadirs of a morphological waveform (e.g., the number of times the slope changes sign from −ve to +ve). Further, all the aforementioned features may be derived from the EGM signal at one or more vectors within a time-window of a pre-specified width such as 200 milliseconds, starting on a ventricular/biventricular paced event.

Figure 11:
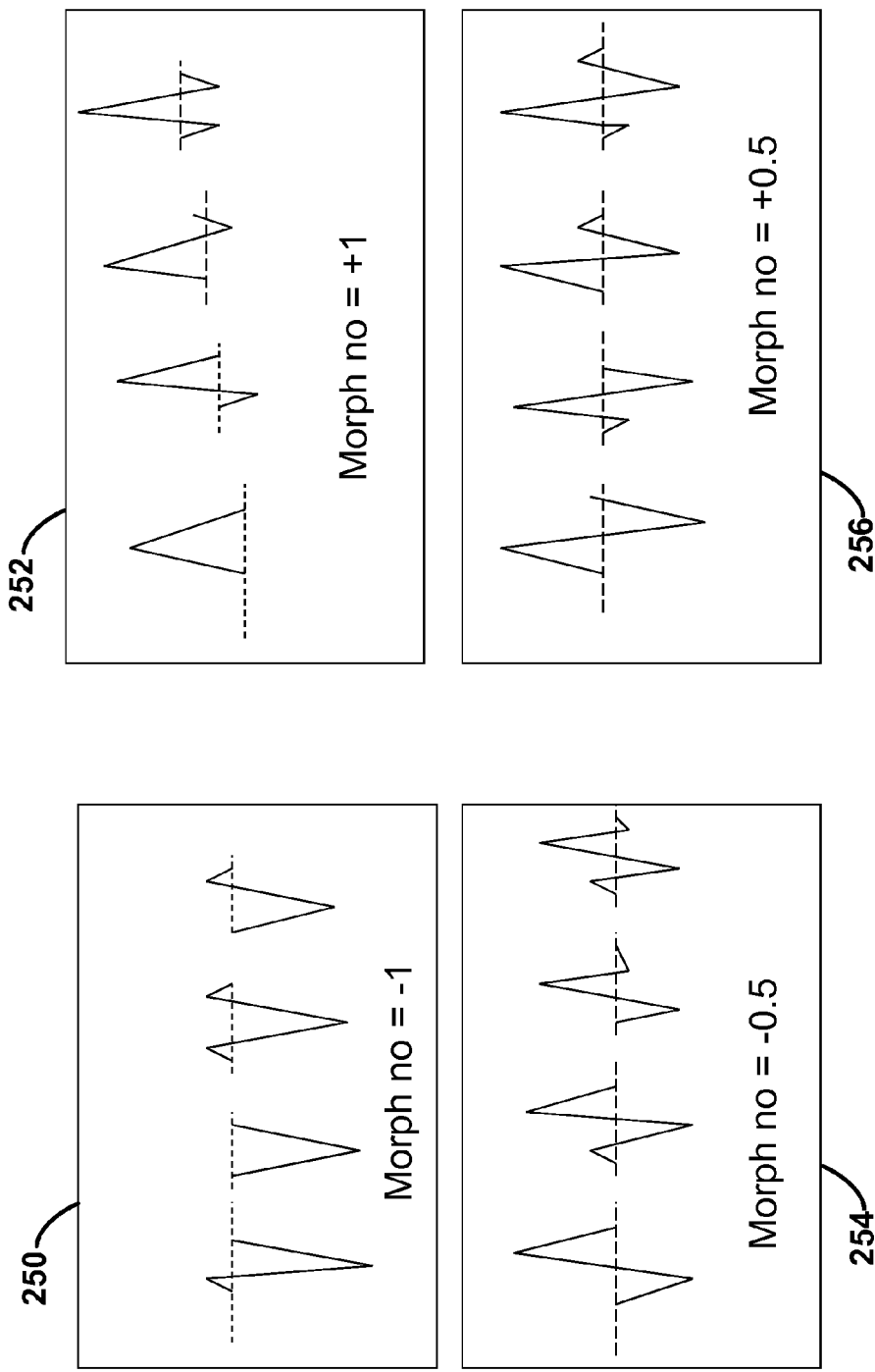
FIG. 11 depicts four broad morphological descriptors for use in classifying morphological waveforms.

Exemplary broad morphological descriptors (BMD) for a SVC electrode to housing electrode vector or a RV defibrillation coil to housing electrode vector are depicted in FIG. 11. Each BMD depicted in FIG. 11 may be described in terms of the absolute values of the maximum and minimum values, the lesser of the absolute values of the maximum and minimum values, and the timing of each of the maximum and minimum values. BMD 250 (Morph no.=−1), which is indicative of a fully paced beat, or an effectively pace beat, may be characterized as having the lesser of the absolute value of the maximum and minimum values being less than 0.11 and the absolute value of the minimum value being greater than the absolute value of the maximum value. BMD 252 (Morph no.=+1), which is indicative of a pseudo-fusion, may be characterized as having the lesser of the absolute value of the maximum and minimum values being less than 0.11 and the absolute value of the maximum value being greater than the absolute value of the minimum value. BMD 256 (Morph no.=+0.5), which is indicative of a fusion, may be characterized as having the lesser of the absolute value of the maximum and minimum values being greater than 0.11 and the maximum value occurring before the minimum value. BMD 254

(Morph no.=−0.5), which is indicative of an unknown or other event, may be characterized as having the lesser of the absolute value of the maximum and minimum values being greater than 0.11 and the minimum value occurring before the maximum value.

Figure 12:
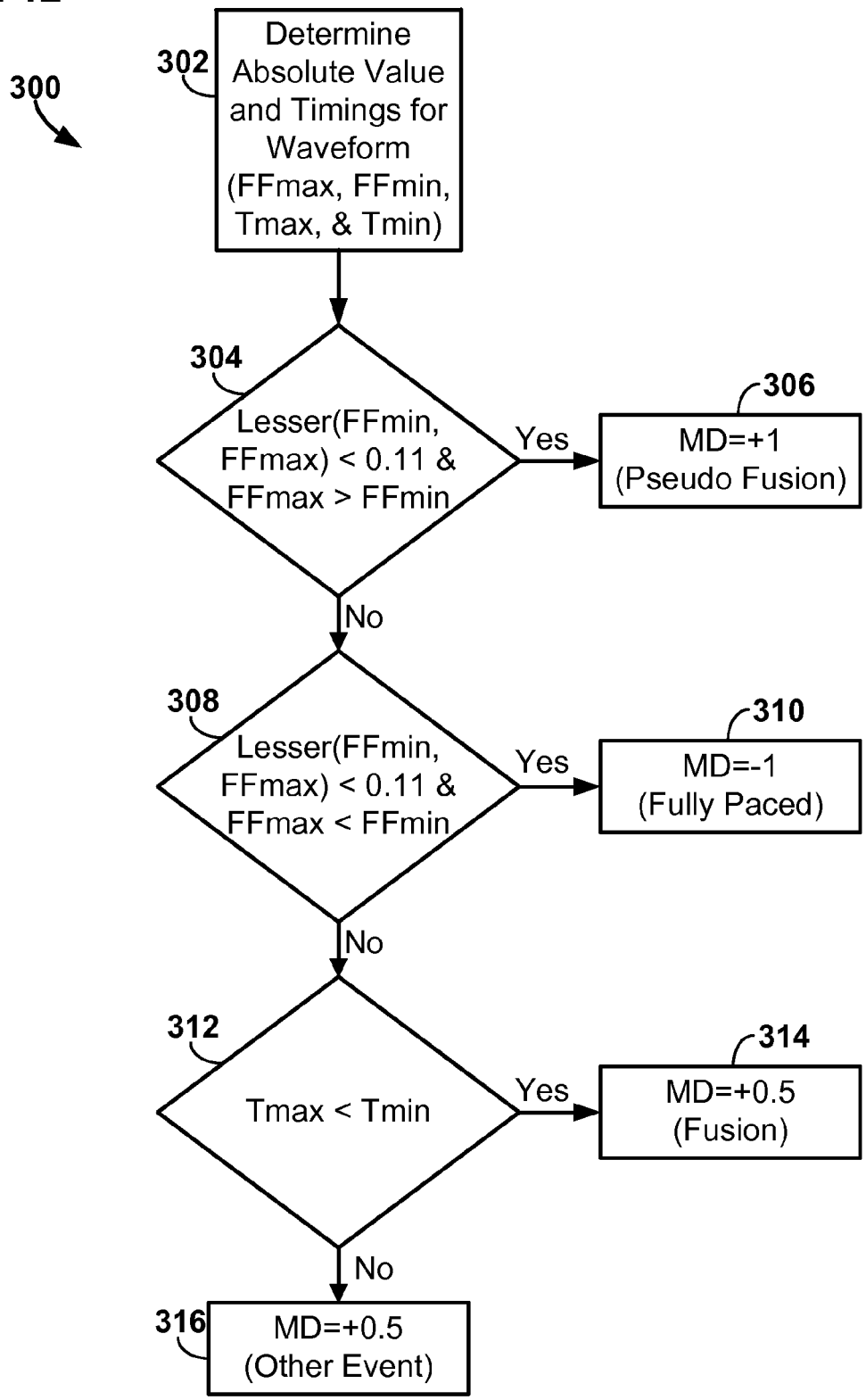
FIG. 12 is a flowchart of an exemplary method for use in classifying morphological waveforms using the broad morphological descriptors of FIG. 11.

An exemplary method 300 using the broad morphological descriptors 250, 252, 254, 256 of FIG. 11 is shown in FIG. 12. At the outset, a vector (e.g., SVC electrode to housing electrode, RV coil electrode to housing electrode, etc.) of the patient's heart may be monitored during pacing therapy for a paced event and a morphological waveform corresponding to a paced event (e.g., corresponding to each paced event such as occurring within a predetermined, or selected, time period, or sensing window, after the delivery of pacing stimulus) is extracted therefrom. From this waveform, the absolute values of the maximum value (FFmax) and the minimum value (FFmin), a max time value representing when the maximum value occurs (Tmax), and a min time value representing when the maximum value occurs (Tmin) may be determined 302. If the lesser of the absolute value of the maximum and minimum values is less than 0.11 and the absolute value of the maximum value is greater than the absolute value of the minimum value 304, then the sensed waveform may be characterized by BMD 252 (Morph no.=+1) and determined to correlate to a pseudo-fusion event 306. If the lesser of the absolute value of the maximum and minimum values is less than 0.11 and the absolute value of the minimum value is greater than the absolute value of the maximum value 308, then the sensed waveform may be characterized by BMD 250 (Morph no.=−1) and determined to correlate to a full paced or effectively paced event 310. If the lesser of the absolute value of the maximum and minimum values is greater than 0.11 and the min time value occurs before the max time value 312, then the sensed waveform may be characterized by BMD 256 (Morph no.=+0.5) and determined to correlate to a fusion event 314. If the lesser of the absolute value of the maximum and minimum values is greater than 0.11 and the max time value occurs before the min time value 312, then the sensed waveform may be characterized by BMD 254 (Morph no.=−0.5) and determined to correlate to an unknown event 316.

Figure 13:
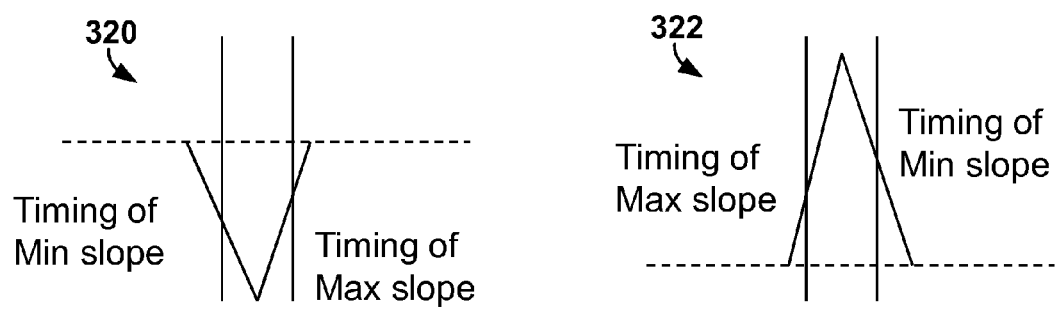
FIGS. 13-14 depict additional features that may be used to classify and/or analyze morphological waveforms.
Figure 14:
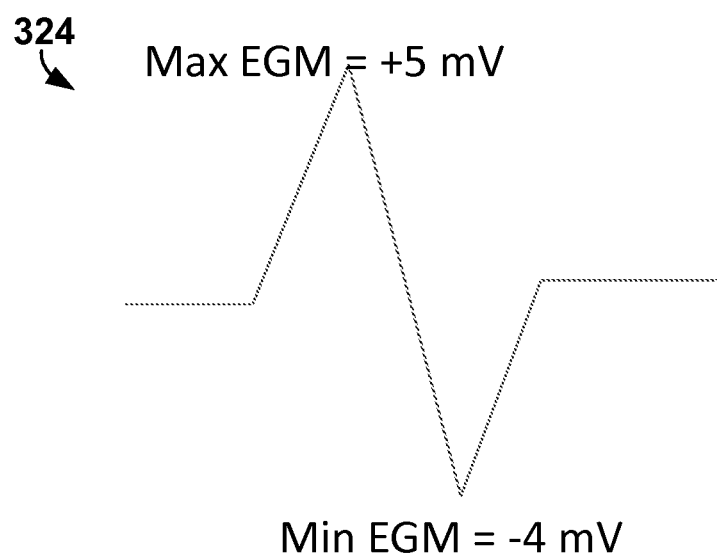

Additional potential features that may be used with the exemplary methods and devices described herein are depicted in FIGS. 13-14. More specifically, the timings of the minimum and maximum slopes are depicted for a positive and a negative waveform in FIG. 13. A slope differential (tsdiff) may be calculated by subtracting the timing of the minimum slope from the maximum slope. As shown, waveform 320 may provide a slope differential greater than zero and waveform 322 may provide a slope differential less than zero. The slope differentials may be computed and used (e.g., as a feature) to analyze waveforms to determine whether each paced event has a predetermined level of effectiveness using the exemplary methods and/or processes described herein.

A maximum value of +5 millivolts and a minimum value of −4 millivolts of waveform 324 are depicted in FIG. 14. An absolute value ratio (r) of the maximum value to the minimum value may be computed and used (e.g., as a feature) to analyze waveforms to determine whether each paced event has a predetermined level of effectiveness using the exemplary methods and/or processes described herein. In this example, the absolute value ratio would be 1.25.

The degree of interaction of paced activation with the intrinsic conduction of the patient (the intrinsic conduction is assumed to be fixed over the short period of time during which this data is collected) may change for different AV delays. Thus, one or more features of a morphological waveform at an electrical vector may vary depending on sensed atrioventricular (AV) delay. As a result, one or more reference features may need to be adjusted, or different reference features entirely may be used, according to the sensed AV delay.

Figure 16:
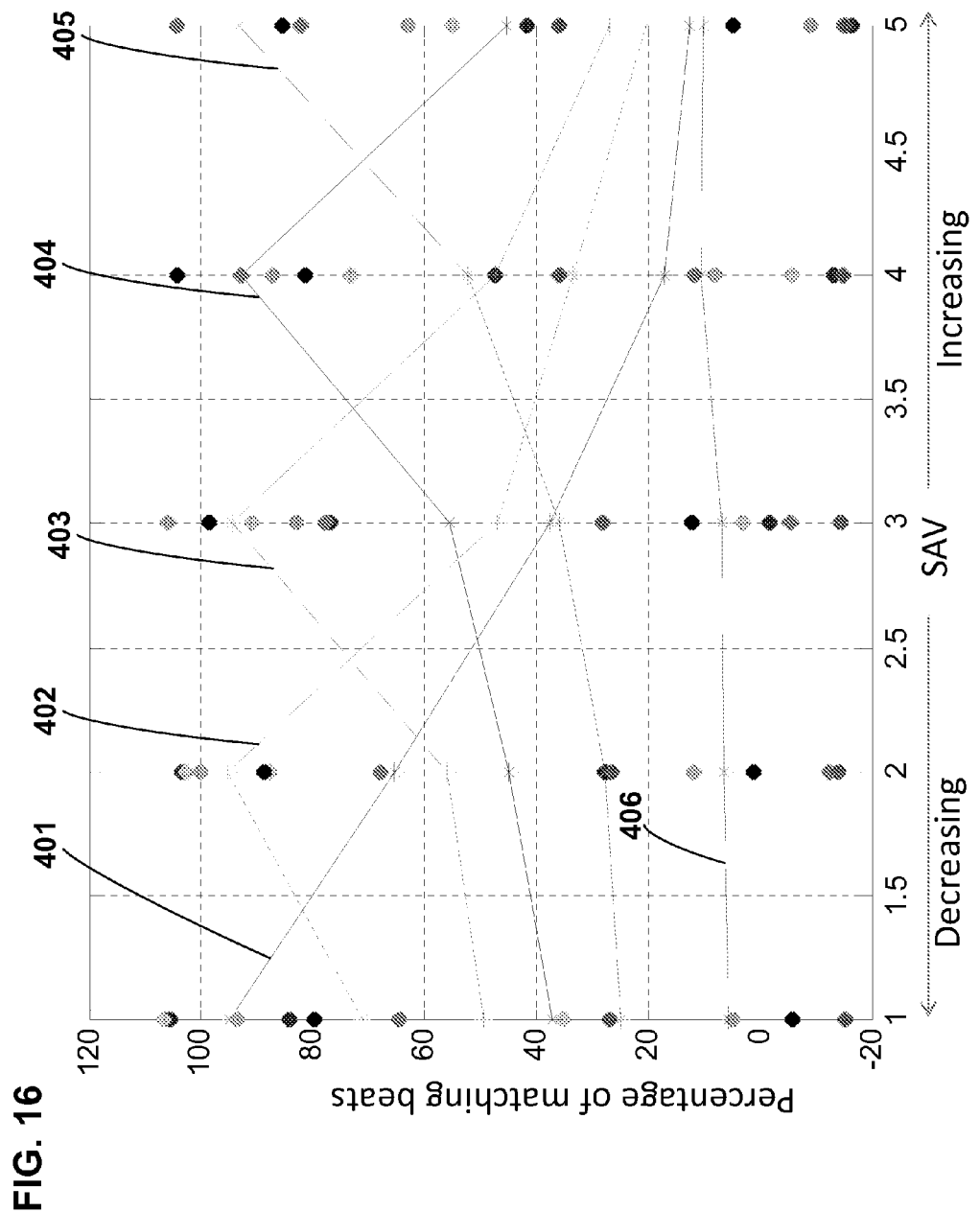
FIG. 16 is a graph of pacing effectiveness ratio versus sensed atrioventricular delay using multiple template features to analyze pacing effectiveness.

A demonstration using data from 52 patients is depicted in FIG. 16. In each patient, biventricular pacing was performed for about 17 to about 30 beats at each of five different AV delays, starting from a short AV delay and incrementing the AV delay by about 20 milliseconds successively by 20 milliseconds.

Multiple sets of reference features were derived, or calibrated, for each different AV delay. The reference features for each different AV delay were then used to determine a pacing effectiveness ratio across multiple arbitrary AV delays (e.g., value 1 on the x axis=20 milliseconds, value 2 on the x axis=40 milliseconds, value 3 on the x axis=60 milliseconds, etc.) as shown in FIG. 16.

The pacing effectiveness ratio using the first set of features is depicted by line 401, the pacing effectiveness ratio using the second set of features is depicted by line 402, the pacing effectiveness ratio using the third set of features is depicted by line 403, the pacing effectiveness ratio using the fourth set of features is depicted by line 404, and the pacing effectiveness ratio using the fifth set of features is depicted by line 405. As shown, the pacing effectiveness ratio using the first set of reference features depicted by line 401 appears to peak with the sensed AV delay of about 1 (e.g., about 20 milliseconds), which, e.g., may be expected since the first set of reference features were calibrated for a sensed AV delay of about 1. Further, as AV delay increases, the pacing effectiveness ratio, or the percentage of matching beats, decreases using the first set of features. The percentage of effectively paced beats using the second set of reference features depicted by line 402 was highest (e.g., about 95%) for a sensed AV delay of 2 but decreased as the sensed AV delay was increased or decreased.

Further, the pacing effectiveness ratio using the third set of reference features depicted using line 403 appears to peak with the sensed AV delay of about 3, the pacing effectiveness ratio using the fourth set of reference features depicted using line 404 appears to peak with the sensed AV delay of about 4, and the pacing effectiveness ratio using the fifth set of reference features depicted using line 405 appear to peak with the sensed AV delay of about 5. Further, a set of reference features depicted using line 406 for natural sinus rhythm are plotted for reference.

If the third set of reference features depicted using line 403 were utilized when the sensed AV delay was 2, then the percentage of matching beats may be determined to be around 55% when it should actually be above 90% (e.g., as shown by the second set of reference features 402). Further, if the first set of reference features depicted using line 401 were utilized when the sensed AV delay was 4, then the percentage of matching beats may be determined to be less than 20% when it should actually be above 90% (e.g., as shown by the second set of reference features depicted using line 402). As a result, the exemplary methods and devices described herein may collect one or more reference sets of features for a plurality of AV delays for each vector (and/or for each event classification type). Further, when analyzing each paced event, the exemplary methods and devices may take the sensed AV delay into account when selecting one or more features to use in the analysis.

As shown, a plurality of sets of reference features, each set for a different sensed AV delay, may be used to track changes in the percentage of effectively paced beats due to changes in AV delay, and thus, potential changes in fusion (e.g., interaction between the paced activation and intrinsic conduction). In the data plotted in FIG. 16, the changes in fusion were simulated by manually changing the AV delay (e.g., while the intrinsic AV conduction remains the same), but in practice, a patient's intrinsic AV conduction may change creating the same effect (e.g., changes in fusion). Such exemplary methods and/or processes using multiple sets of reference features, each for different sensed AV delays, may be used to provide a more useful pacing effectiveness metric, one which takes into account sensed AV delay (e.g., based on a beat-to-beat comparison of electrogram morphologic features to reference features).

In one or more embodiments, although two or more vectors are generally monitored and used to determine pacing effectiveness as described herein, a single specific vector (e.g., by itself) may also be used to determine pacing effectiveness (e.g., one or more features of a reference morphological waveform at a specific vector may be compared to one or more features of a sensed morphological waveform at the specific vector without analyzing waveforms at any other vector).

The techniques described in this disclosure, including those attributed to the IMD 16, the programmer 24, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. A system for tracking effectiveness of pacing therapy to a patient:
    a therapy delivery module configured to deliver pacing therapy to a patient's heart;
    sensing apparatus configured to monitor electrical activity of the patient's heart, wherein the sensing apparatus comprises a plurality of electrodes;
    a sensing module coupled to the sensing apparatus and configured to monitor two or more electrical vectors of the patient's heart using the plurality of electrodes of the sensing apparatus during pacing therapy; and
    a control module coupled to the therapy delivery module and to the sensing module and configured to:
    initiate the delivery of pacing therapy to the patient's heart over a plurality of heartbeats,
    monitor two or more electrical vectors of the patient's heart during pacing therapy for each paced event of a plurality of paced events occurring over a period of time, wherein monitoring the two or more electrical vectors comprises sensing a morphologic waveform corresponding to the paced event at each electrical vector of the two or more electrical vectors using a different pair of electrodes of the plurality of electrodes,
    analyze whether each paced event of the plurality of paced events has a predetermined level of effectiveness based on at least one feature of the sensed morphologic waveform for each electrical vector of the two or more monitored electrical vectors, and
    track a pacing effectiveness ratio, the pacing effectiveness ratio being the ratio between the amount of paced events over time having a predetermined level of effectiveness and the number of paced events.

2. The system of claim 1, wherein the control module is further configured to collect at least one reference feature of a reference morphological waveform corresponding to a known effectively paced event for each electrical vector of the two or more monitored electrical vectors, and
    wherein, to analyze whether each paced event of the plurality of paced events has a predetermined level of effectiveness, the control module is further configured to compare the at least one feature of the sensed morphological waveform to the at least one feature of the reference morphological waveform.

3. The system of claim 2, wherein the control module is further configured to collect at least one reference feature of a reference morphological waveform corresponding to a known effectively paced event for a plurality of sensed atrio-ventricular delays for each electrical vector of the two or more monitored electrical vectors.

4. The system of claim 1, wherein the at least one feature comprises:
    an absolute value of a maximum value of the sensed morphological waveform; and
    an absolute value of a minimum value of the sensed morphological waveform, and
    wherein, to analyze whether each paced event of the plurality of paced events has a predetermined level of effectiveness, the control module is further configured to classify the paced event as an effectively paced event if, for each electrical vector of the two or more electrical vectors:
    the lesser of the absolute value of the maximum value and the absolute value of value of the minimum value is less than a selected threshold value; and
    the absolute value of the minimum value is greater than the absolute value of value of the maximum value.

5. The system of claim 1, wherein the at least one feature comprises:

an absolute value of a maximum value of the sensed morphological waveform;

an absolute value of a minimum value of the sensed morphological waveform;

a max time value representing when a maximum value of the sensed morphological waveform occurs; and a min time value representing when a minimum value of the sensed morphological waveform occur; and wherein, to analyze whether each paced event of the plurality of paced events has a predetermined level of effectiveness, the control module is further configured to classify the paced event as one of an effectively paced event, a pseudo-fusion event, a fusion event, and an unknown event based on one or more of the absolute value of the maximum value, the absolute value of the minimum value, the max time value, and the min time value.

6. The system of claim 5, wherein, to analyze whether each paced event of the plurality of paced events has a predetermined level of effectiveness, the control module is further configured to classify the paced event as a pseudo-fusion event if, for each electrical vector of the two or more electrical vectors:

the lesser of the absolute value of the maximum value and the absolute value of value of the minimum value is less than a selected threshold value, and the absolute value of the maximum value is greater than the absolute value of value of the minimum value; and wherein the control module is further configured to track an amount of pseudo-fusion events over time;

wherein, to analyze whether each paced event of the plurality of paced events has a predetermined level of effectiveness, the control module is further configured to classify the paced event as a fusion event if, for each electrical vector of the two or more electrical vectors:

the lesser if the absolute value of the maximum value and the absolute value of value of the minimum value is greater than a selected threshold value, and the max time value occurs before the min time value; and wherein the control module is further configured to track an amount of fusion events.

7. The system of claim 5, wherein, to analyze whether each paced event of the plurality of paced events has a predetermined level of effectiveness, the control module is further configured to classify the paced event as an effectively paced event if, for each electrical vector of the two or more electrical vectors:

a ratio of the absolute value of the maximum value to the absolute value of the minimum value is less than or equal to 2, and the max time value occurs before the min time value.

8. The system of claim 1, wherein each electrode of the different pairs of electrodes used to sense the two or more electrical vectors are not used for pacing therapy.

9. The system of claim 1, wherein the control module is further configured to initiate an alert if the effectiveness ratio drops below an effectiveness threshold value over a selected period of time.

10. The system of claim 1, wherein at least one electrical vector of the two or more electrical vectors is sensed using an electrode located proximate the patient's right ventricle and a housing electrode located on a housing of the implantable medical device.

11. A method of tracking effectiveness of pacing therapy provided using an implantable medical device, wherein the method comprises:

delivering pacing therapy to a patient's heart using one or more pacing electrodes of an implantable medical device, wherein the pacing therapy is delivered over a plurality of heartbeats;

monitoring two or more electrical vectors of the patient's heart during pacing therapy for each paced event of a plurality of paced events occurring over a period of time, wherein monitoring the two or more electrical vectors comprises sensing a morphologic waveform corresponding to the paced event at each electrical vector of the two or more electrical vectors using a different pair of electrodes of the implantable medical device;

analyzing, using the implantable medical device, whether each paced event of the plurality of paced events has a predetermined level of effectiveness based on at least one feature of the sensed morphologic waveform for each electrical vector of the two or more monitored electrical vectors; and tracking, using the implantable medical device, a pacing effectiveness ratio, the pacing effectiveness ratio being the ratio between the amount of paced events over time having a predetermined level of effectiveness and the number of paced events.

12. The method of claim 11, wherein the method further comprises collecting at least one reference feature of a reference morphological waveform corresponding to a known effectively paced event for each electrical vector of the two or more monitored electrical vectors, and wherein analyzing whether each paced event of the plurality of paced events has a predetermined level of effectiveness comprises comparing the at least one feature of the sensed morphological waveform to the at least one feature of the reference morphological waveform.

13. The method of claim 12, wherein the method further comprises collecting at least one reference feature of a reference morphological waveform corresponding to a known effectively paced event for a plurality of sensed atrioventricular delays for each electrical vector of the two or more monitored electrical vectors.

14. The method of claim 11, wherein the at least one feature comprises:

an absolute value of a maximum value of the sensed morphological waveform; and an absolute value of a minimum value of the sensed morphological waveform, and wherein analyzing whether each paced event of the plurality of paced events has a predetermined level of effectiveness comprises classifying the paced event as an effectively paced event if, for each electrical vector of the two or more electrical vectors:

the lesser of the absolute value of the maximum value and the absolute value of value of the minimum value is less than a selected threshold value, and the absolute value of the minimum value is greater than the absolute value of value of the maximum value.

15. The method of claim 11, wherein the at least one feature comprises:

an absolute value of a maximum value of the sensed morphological waveform;

an absolute value of a minimum value of the sensed morphological waveform;

a max time value representing when a maximum value of the sensed morphological waveform occurs; and a min time value representing when a minimum value of the sensed morphological waveform occurs; and wherein analyzing whether each paced event of the plurality of paced events has a predetermined level of effectiveness comprises classifying the paced event as one of an effectively paced event, a fusion event, a pseudo-fusion event, and an unknown event based on one or more of the absolute value of the maximum value, the absolute value of the minimum value, the max time value, and the min time value.

16. The method of claim 15, wherein analyzing whether each paced event of the plurality of paced events has a predetermined level of effectiveness comprises classifying the paced event as a pseudo-fusion event if, for each electrical vector of the two or more electrical vectors:
the lesser of the absolute value of the maximum value and the absolute value of value of the minimum value is less than a selected threshold value, and
the absolute value of the maximum value is greater than the absolute value of value of the minimum value; and
wherein the method further comprises tracking an amount of pseudo-fusion events over time; and
wherein analyzing whether each paced event of the plurality of paced events has a predetermined level of effectiveness comprises classifying the paced event as a fusion event if, for each electrical vector of the two or more electrical vectors:
the lesser magnitude of the minimum value and the maximum value of the electrical vector is greater than a selected threshold value and
the minimum value of the electrical vector occurs before the maximum value of the electrical vector; and
wherein the method further comprises tracking an amount of fusion events.

17. The method of claim 15, wherein analyzing whether each paced event of the plurality of paced events has a predetermined level of effectiveness comprises classifying the paced event as having a predetermined level of effectiveness if, for each electrical vector of the two or more electrical vectors:
a ratio of the absolute value of the maximum value to the absolute value of the minimum value is less than or equal to 2; and
the max time value occurs before the min time value.

18. The method of claim 11, wherein each electrode of the different pairs of electrodes used to sense the two or more electrical vectors are not used for pacing therapy.

19. The method of claim 11, wherein the method further comprises initiating an alert if the effectiveness ratio drops below an effectiveness threshold value over a selected period of time.

20. The method of claim 11, wherein at least one electrical vector of the two or more electrical vectors is sensed using an electrode located proximate the patient's right ventricle and a housing electrode located on a housing of the implantable medical device.

* * * * *